(12) United States Patent
Weisshaupt et al.

(10) Patent No.: US 9,388,080 B2
(45) Date of Patent: Jul. 12, 2016

(54) PERMANENT FILTER FOR A STERILIZATION CONTAINER, STERILIZATION CONTAINER AND METHOD FOR PRODUCING A PERMANENT FILTER

(71) Applicant: Aesculap AG, Tuttlingen (DE)

(72) Inventors: Dieter Weisshaupt, Immendingen (DE); Thomas Weik, Tuttlingen (DE); Stefan Schuster, Villingen-Schwenningen (DE); John Gray-Dreizler, Rottweil (DE); Wolfgang Burger, Plochingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/529,570

(22) Filed: Oct. 31, 2014

(65) Prior Publication Data
US 2015/0125361 A1    May 7, 2015

(30) Foreign Application Priority Data
Nov. 5, 2013   (DE) .......................... 10 2013 112 129

(51) Int. Cl.
*A61L 9/00*    (2006.01)
*C09K 3/22*    (2006.01)
*B01D 46/00*    (2006.01)
(Continued)

(52) U.S. Cl.
CPC ................. *C04B 35/117* (2013.01); *A61L 2/16* (2013.01); *A61L 2/26* (2013.01); *B01D 39/2075* (2013.01); *C04B 35/10* (2013.01); *C04B 35/111* (2013.01); *C04B 35/64* (2013.01); *C04B 2235/3206* (2013.01); *C04B 2235/3217* (2013.01); *C04B 2235/3418* (2013.01); *C04B 2235/70* (2013.01)

(58) Field of Classification Search
CPC ............... A61L 9/00; A61L 9/01; A61L 9/03; A61K 2300/00; C12N 2310/321
USPC ................... 422/5, 311; 95/273, 285; 55/523; 252/88.2; 424/68
See application file for complete search history.

(56) References Cited

U.S. PATENT DOCUMENTS 4,407,967 A   10/1983  Luks
5,202,098 A   4/1993   Nichols
(Continued)

FOREIGN PATENT DOCUMENTS

DE   298 19 825    3/1999
DE   19851239      5/2000
(Continued)

*Primary Examiner* — Monzer R Chorbaji
(74) *Attorney, Agent, or Firm* — Lipsitz & McAllister, LLC

(57) ABSTRACT

A permanent filter for a medical sterilization container is provided. The permanent filter is made from a ceramic. The ceramic is made from globular substrate grains. A medical sterilization container is also provided, in particular for receiving and storing objects to be sterilized, having a container bottom part and a container top part for closing the container bottom part in a closed position of the sterilization container. At least one of the container bottom part and the container top part have a gas exchange orifice, which is closed with a permanent filter. The permanent filter is made from a ceramic and the ceramic is made from globular substrate grains. In addition, a method is provided for producing a permanent filter for a medical sterilization container. The permanent filter is produced from a ceramic material by sintering. Globular substrate grains are used as the ceramic material.

25 Claims, 16 Drawing Sheets

(51) Int. Cl.
*C04B 35/117* (2006.01)
*A61L 2/16* (2006.01)
*B01D 39/20* (2006.01)
*C04B 35/10* (2006.01)
*C04B 35/111* (2006.01)
*C04B 35/64* (2006.01)
*A61L 2/26* (2006.01)

(56) References Cited

U.S. PATENT DOCUMENTS

| | | |
|---|---|---|
| 5,236,595 A | 8/1993 | Wang et al. |
| 5,474,679 A | 12/1995 | Nichols et al. |
| 5,474,738 A | 12/1995 | Nichols et al. |
| 6,048,503 A | 4/2000 | Riley et al. |
| 6,165,437 A | 12/2000 | Mohri et al. |
| 6,217,835 B1 | 4/2001 | Riley et al. |
| 6,247,609 B1 | 6/2001 | Gabele et al. |
| 6,715,628 B1 | 4/2004 | Nichols et al. |
| 6,758,970 B1 | 7/2004 | Nurminen et al. |
| 6,889,832 B2 | 5/2005 | Gabele |
| 2002/0098138 A1 | 7/2002 | Gabele |

FOREIGN PATENT DOCUMENTS

| | | | |
|---|---|---|---|
| EP | 0 152 544 | 3/1995 | |
| EP | 0644279 | 3/1995 | |
| JP | EP 0 644 279 A1 * | 3/1995 | ............... C30B 29/20 |
| WO | 01/08583 | 2/2001 | |

* cited by examiner

Fig. 6
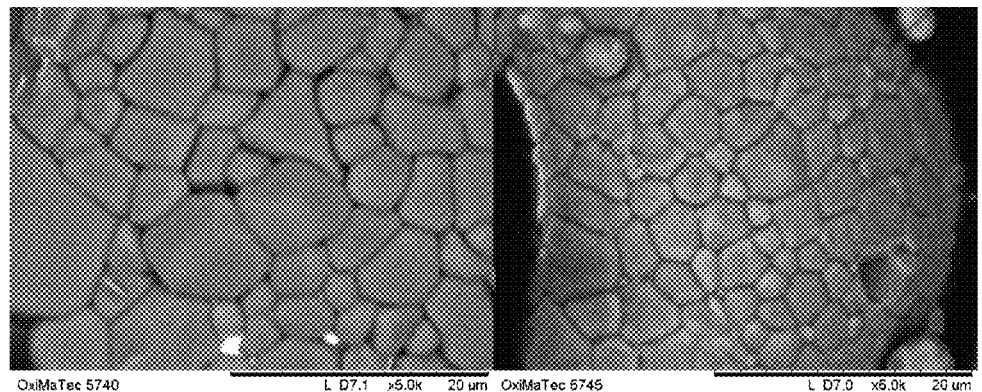
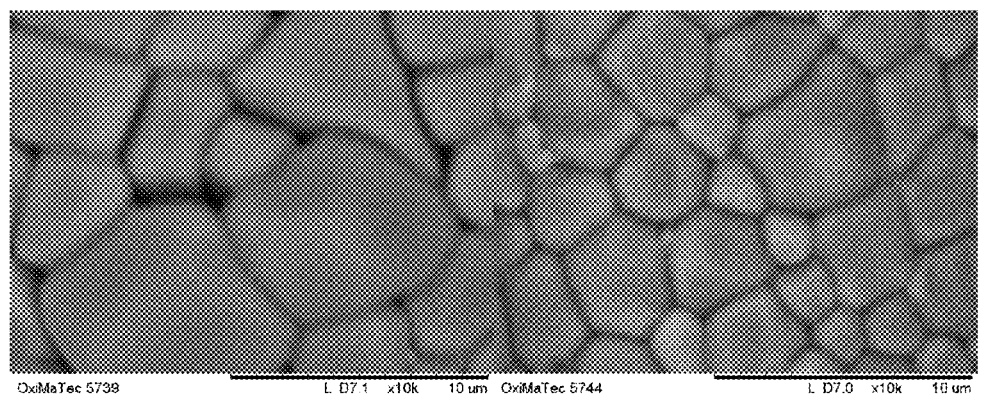
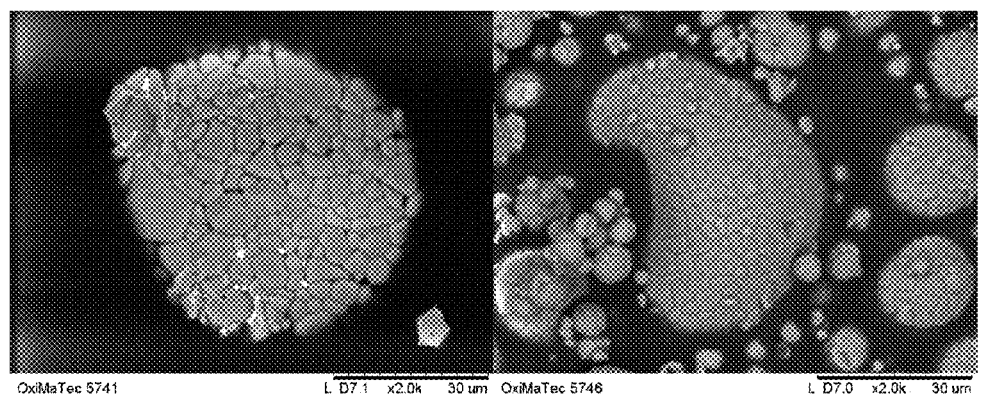

Fig. 7
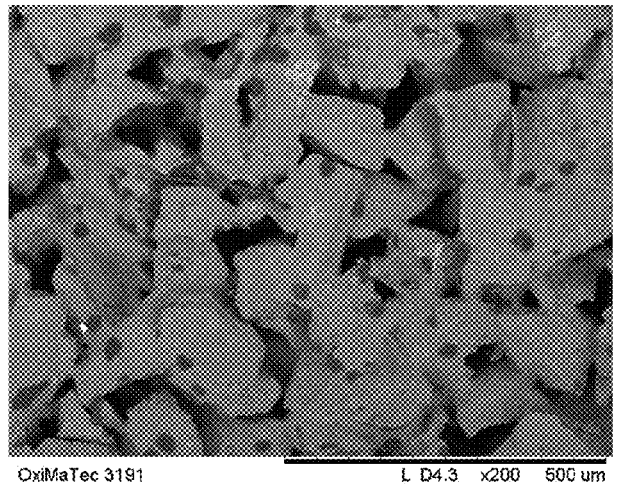
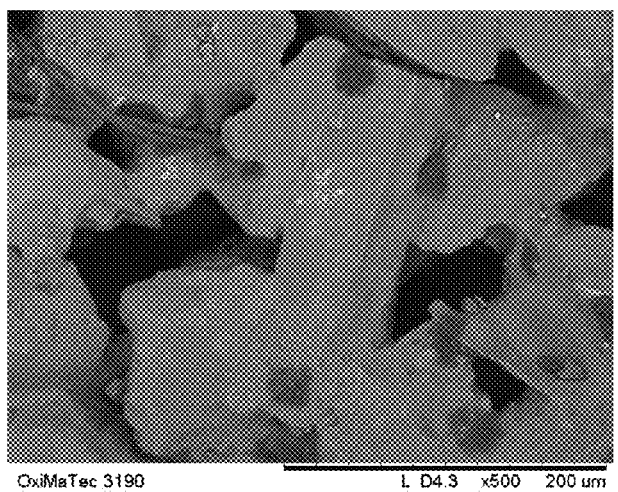
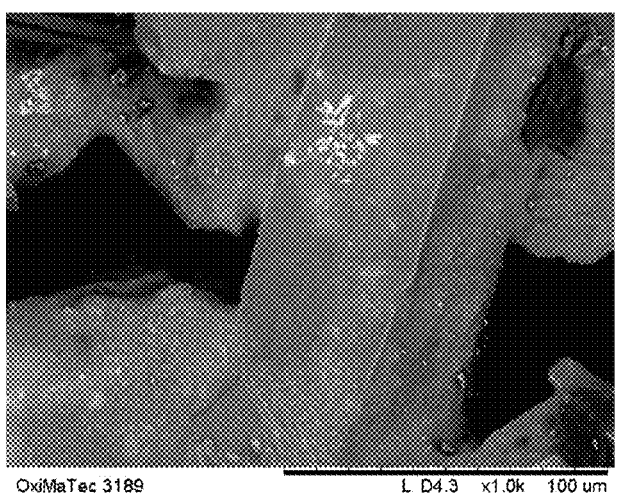

Fig. 8
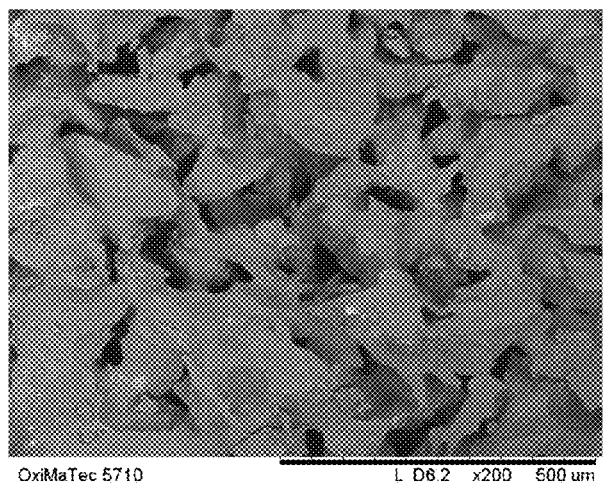
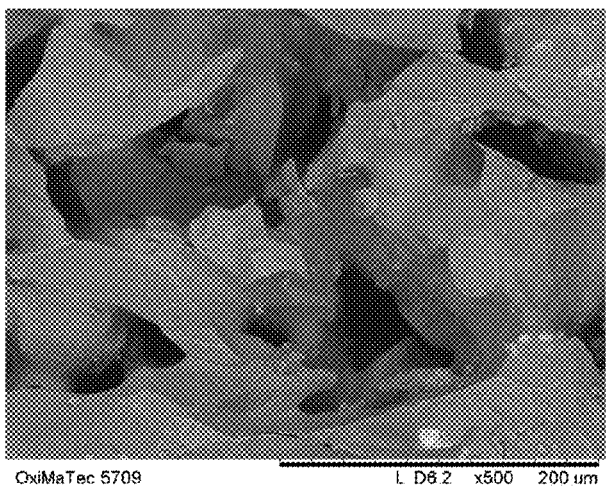
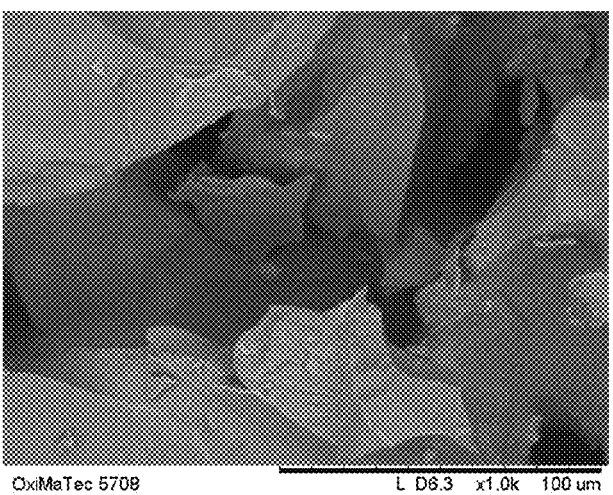

Fig. 9
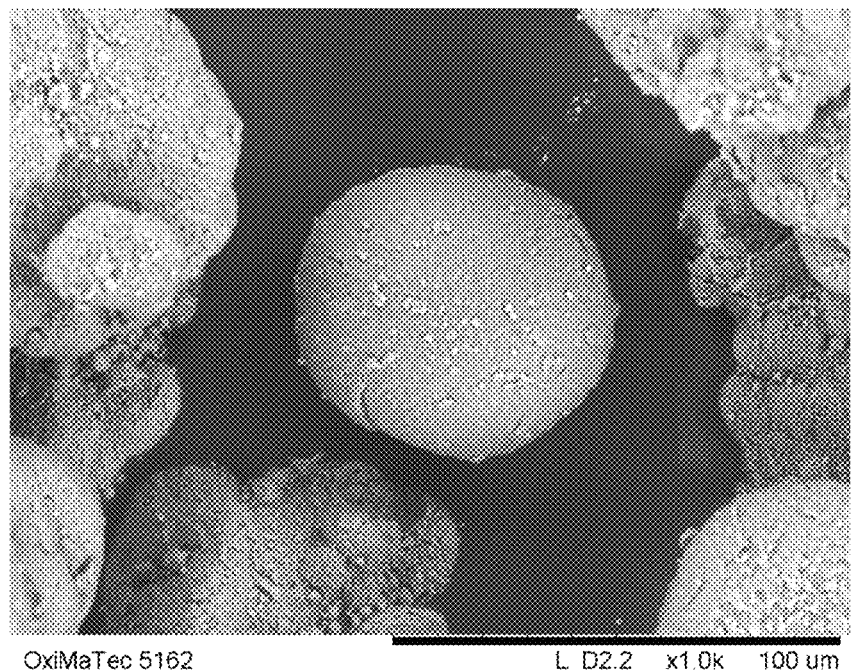
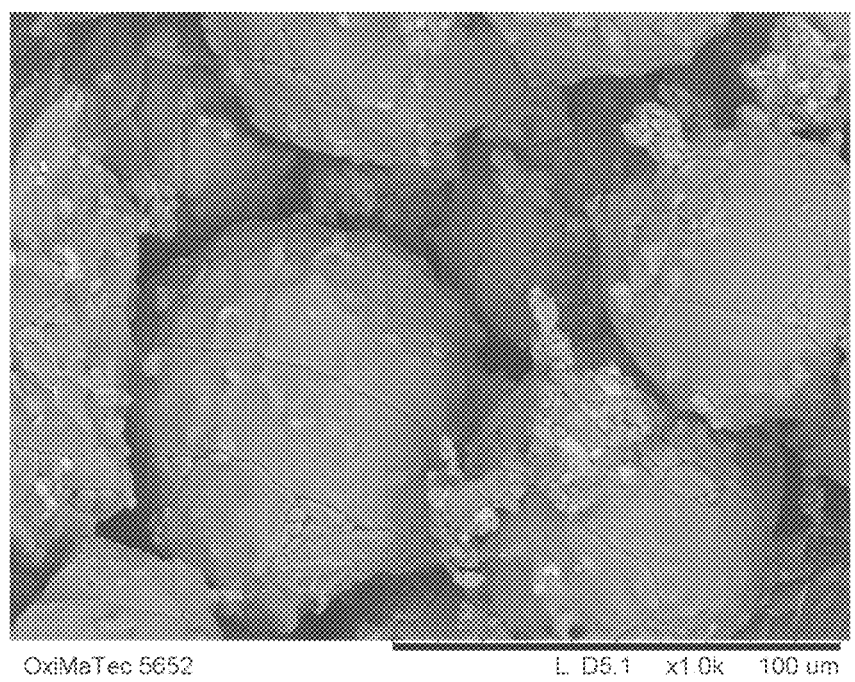

Fig. 10
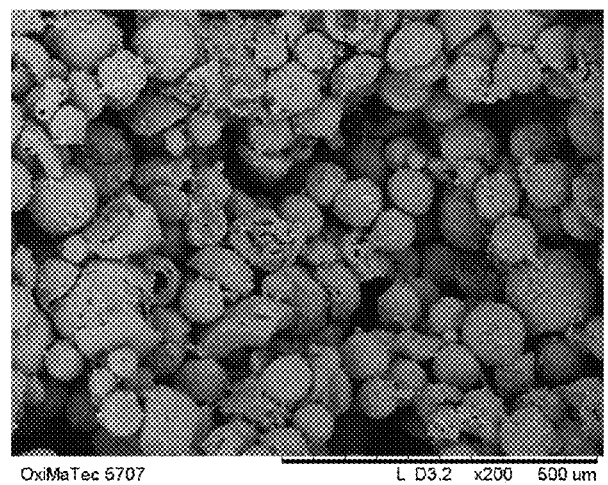
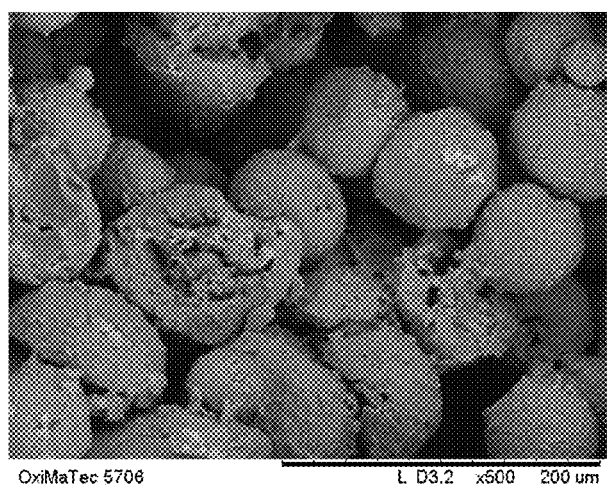
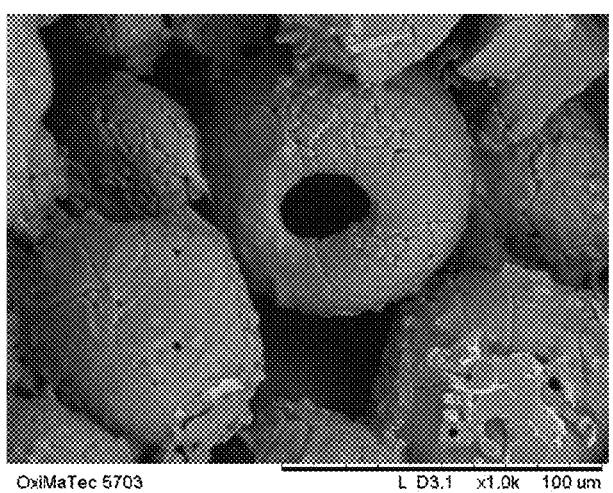

Fig. 11
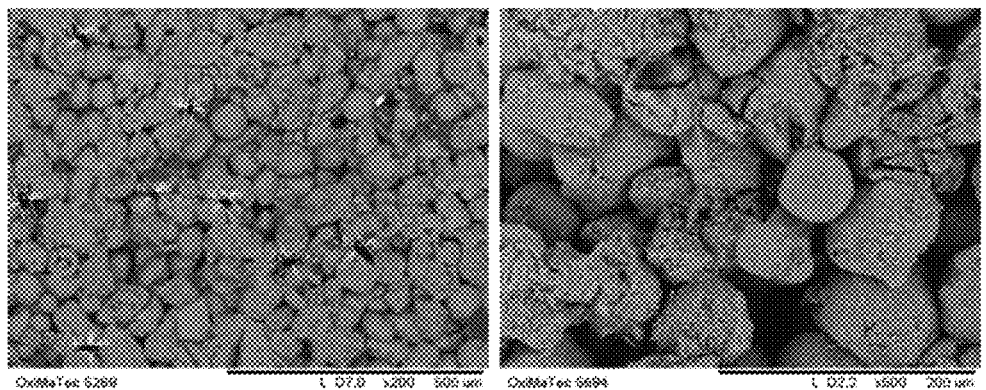
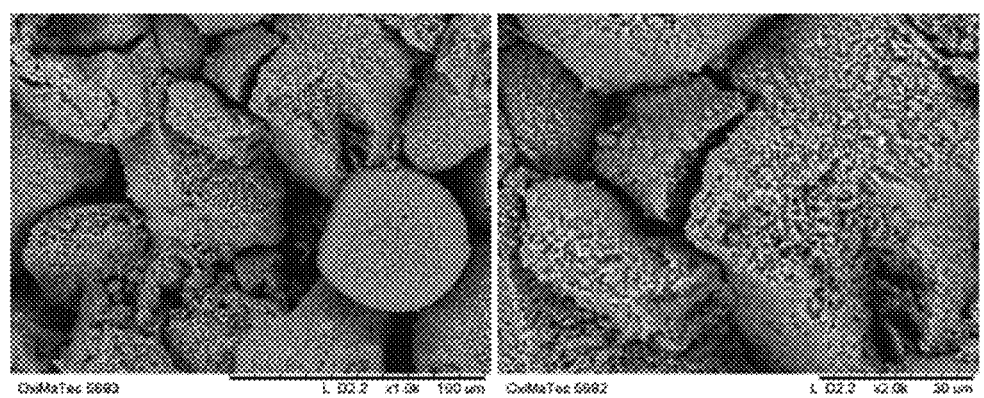

Fig. 15
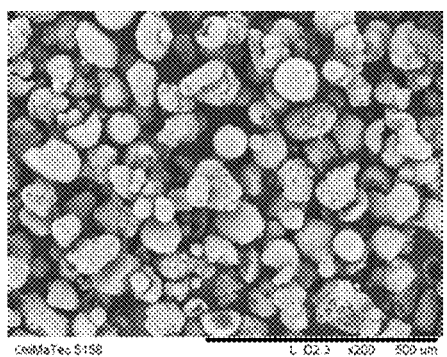 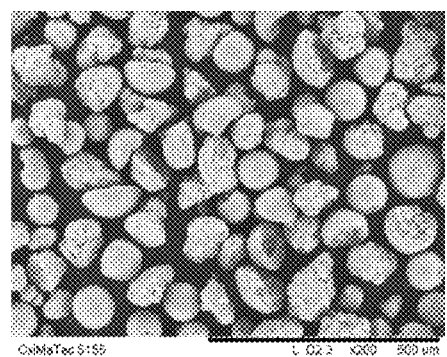
Fig. 16
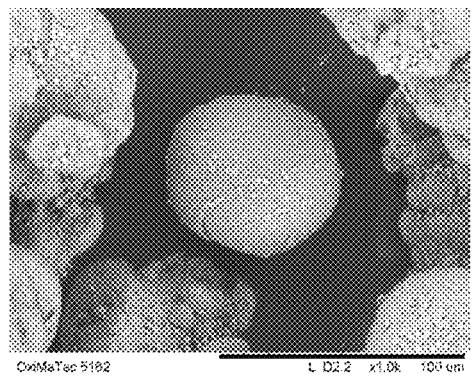 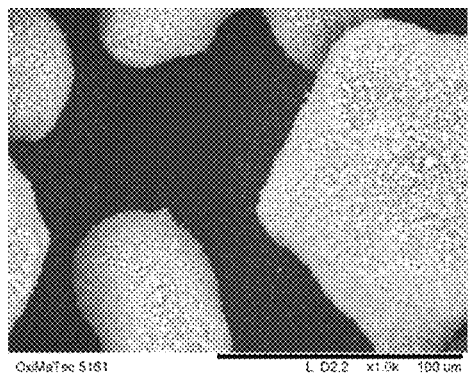

PERMANENT FILTER FOR A STERILIZATION CONTAINER, STERILIZATION CONTAINER AND METHOD FOR PRODUCING A PERMANENT FILTER

CROSS-REFERENCE TO RELATED APPLICATIONS

This application claims the benefit of German patent application number 10 2013 112 129.2 filed on Nov. 5, 2013, which is incorporated by reference herein in its entirety and for all purposes.

FIELD OF THE INVENTION

The present invention relates to permanent filters generally, and more specifically to a permanent filter for a medical sterilization container.

Furthermore, the present invention relates to medical sterilization containers generally, and more specifically to a medical sterilization container, in particular for receiving and storing objects to be sterilized, with a container bottom part and a container top part for closing the container bottom part in a closed position of the sterilization container, the sterilization container defining a container interior, which is defined by the container bottom part and by the container top part, and wherein the container bottom part and/or the container top part have a gas exchange orifice, which is closed with a permanent filter.

Furthermore, the present invention relates to methods for producing a permanent filters generally, and more specifically to a method for producing a permanent filter for a medical sterilization container.

BACKGROUND OF THE INVENTION

Sterilization containers with permanent filters made of a plastics material, in particular polytetrafluoroethylene, are known for example from DE 298 19 825 U1. They are used instead of conventional disposable filters, in particular paper filters, in sterilization containers to close gas exchange orifices. Although such plastics filters meet the requirements of porosity and pore size, they display weaknesses with regard to resterilizability.

SUMMARY OF THE INVENTION

In a first aspect of the invention, a permanent filter for a medical sterilization container is provided. The permanent filter is made from a ceramic. The ceramic is made from globular substrate grains.

In a second aspect of the invention, a medical sterilization container, in particular for receiving and storing objects to be sterilized, has a container bottom part and a container top part for closing the container bottom part in a closed position of the sterilization container. The sterilization container defines a container interior, which is delimited by the container bottom part and by the container top part. The container bottom part and/or the container top part have a gas exchange orifice, which is closed with a permanent filter. The permanent filter is made from a ceramic and the ceramic is made from globular substrate grains.

In a third aspect of the invention, a method for producing a permanent filter for a medical sterilization container is provided. The permanent filter is produced from a ceramic material by sintering. Globular substrate grains are used as the ceramic material.

BRIEF DESCRIPTION OF THE DRAWINGS

The foregoing summary and the following description may be better understood in conjunction with the drawing figures, of which:

FIG. 6: $\gamma$-$Al_2O_3$ (1650° C., left), $\alpha$-$Al_2O_3$ (1650° C., right);

FIG. 7: SEM images of surfaces of a ceramic of aluminium oxide grains, so-called fused corundum, in the stated magnifications;

FIG. 8: SEM images of fracture facets of the ceramic of FIG. 7;

FIG. 9: SEM images at a calcination temperature $T_{calc}$=1300° C. (top) and $T_{calc}$=1450° C. (bottom);

FIG. 10: SEM fracture images of the microstructure of a permanent filter;

FIG. 11: SEM images of V0500;

FIG. 15: Screening fraction 106-90 μm; left before calcination and right after calcination;

FIG. 16: Calcination product without (left) and with (right) alumina;

DETAILED DESCRIPTION OF THE INVENTION

Figure 1:
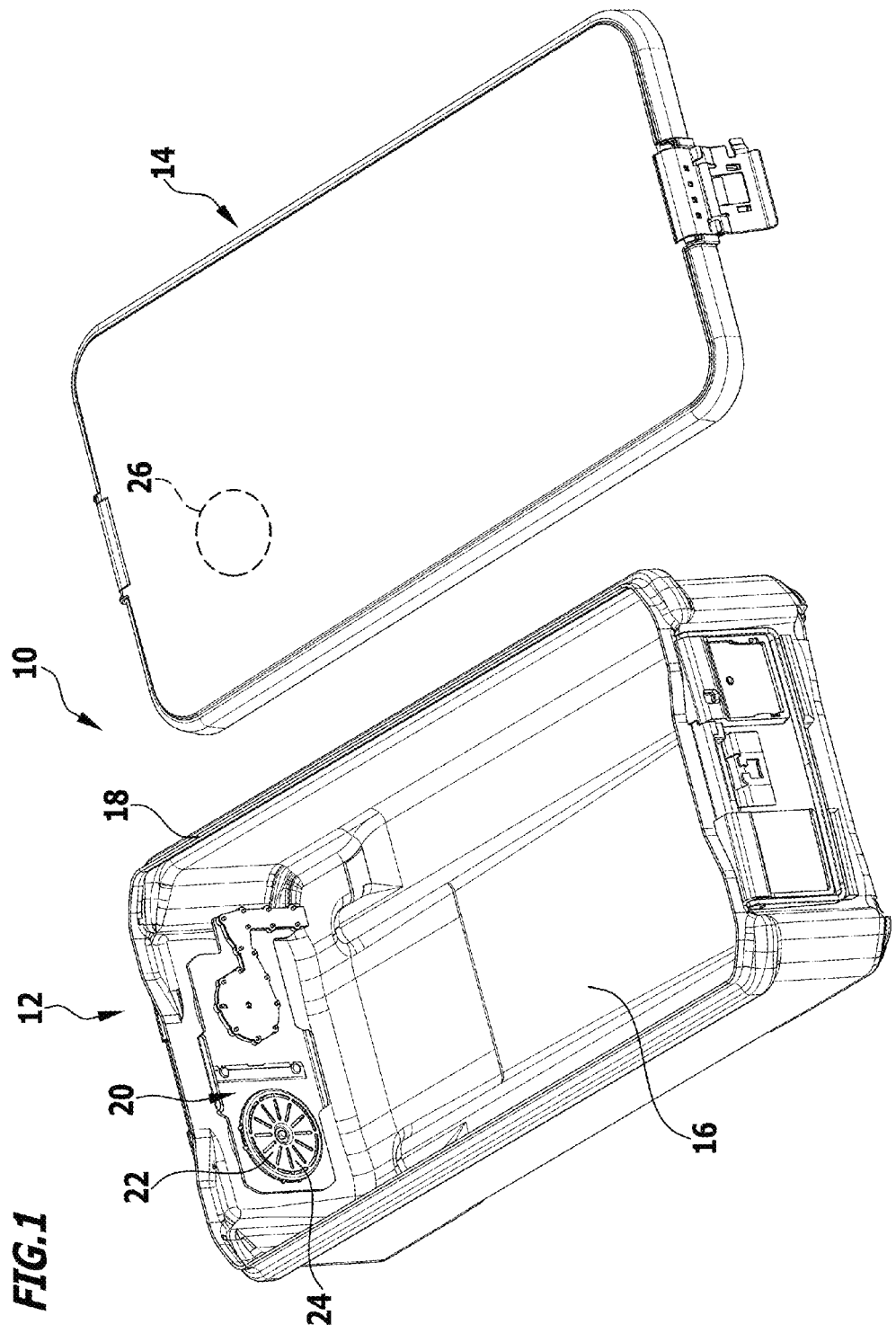
FIG. 1: is a schematic representation of a first exemplary embodiment of a sterilization container with a container bottom part and a container top part and a permanent filter.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a permanent filter for a medical sterilization container, wherein the permanent filter is made from a ceramic and wherein the ceramic is made from globular substrate grains.

Such a ceramic permanent filter has the desired bioinertness and biocompatibility to be able to serve in particular for medical sterilization containers. Furthermore, the globular, i.e. spherical or substantially spherical or spheroidal substrate grains allow the porosity and pore size of the permanent filter to be adjusted as desired. Compared with ceramic substrates of powders or other non-globular grains, globular substrate grains have the advantage that the porosity and thus also the permeability of the permanent filter can be markedly better adjusted. A ceramic permanent filter in particular allows use as a bacteriological barrier and saturated steam sterilizability. Conditions for this purpose may in particular be a pressure of 4 bar and a sterilization temperature of 143° C. Ceramic permanent filters are suitable for filtering steam and air, allow flow on both sides of the filter and are additionally germ-proof according to DIN 58953. Unlike with fused ceramic materials, which may for example be sintered to form the permanent filter, with globular substrate grains defined pores are obtained. Porosity may thus also be simply adjusted as a function of a size of the globular substrate grains. Globular substrate grains in particular have the advantage that they can be arranged in a relatively defined manner and a porosity may be adjusted in a defined manner as a function of a diameter of the substrate grains.

The permanent filter is preferably configured to be self-supporting without a support element. A self-supporting permanent filter allows the complete filter area to be used. Furthermore, contamination of a support or support material may also be prevented in this way. Overall, a self-supporting permanent filter allows minimization of both the number and the areas of gas exchange orifices on sterilization containers.

It is advantageous for the substrate grains to be produced by dispersing and deagglomerating ceramic powder in aqueous suspension to produce individual primary grains, spray drying the suspension containing the primary grains and calcining the primary grains to yield secondary grains, which form the globular substrate grains. By calcining the primary grains to yield secondary grains, it is in particular possible to form globular substrate grains. A specific permeability is necessary in particular for a minimum throughput of air and/or steam through the permanent filter. Globular substrate grains may be formed in the desired size and quality in the manner described.

It is particularly advantageous for the ceramic powder to be aluminium oxide ($Al_2O_3$), zirconium oxide ($ZrO_2$), titanium dioxide ($TiO_2$), mullite, silicate, kaolin or any desired mixture thereof. The stated materials have the required properties with regard to bioinertness and biocompatibility, which allow the required resterilizability of the permanent filter.

The ceramic powder is favourably γ-aluminium oxide (γ-$Al_2O_3$). This aluminium oxide modification may be put to excellent use as a starting material, since it may be further processed or treated in a specific manner, in particular to form a stable α-aluminium oxide (α-$Al_2O_3$) modification.

The globular substrate grains are preferably produced by calcination of γ-aluminium oxide (γ-$Al_2O_3$) into α-aluminium oxide (α-$Al_2O_3$). Formation of the stable α-aluminium oxide modification can be most simply achieved by using γ-aluminium oxide as starting material. In addition, stable globular substrate grains can in particular be formed in this way.

To be able to ensure the highest possible quality of α-aluminium oxide formed, it is favourable for the globular substrate grains to be produced by calcination at temperatures of at least around 1100° C. It is advantageous, in particular, for calcination to proceed at a temperature in a range from around 1300° C. to around 1500° C. It is favourable to perform calcination at around 1350° C. Microporosity of the globular substrate grains is in particular obtained as a function of temperature. For example, the higher the temperature, the lower the microporosity. At calcination temperatures of at least 1400° C. for example practically impermeable, i.e. non-porous, globular substrate grains of γ-aluminium oxide may be formed.

To form a durably stable permanent filter, it is advantageous for it to be produced by sintering at temperatures in the range from around 1350° C. to around 1700° C. Sintering is preferably performed at temperatures in a range from around 1390° C. to around 1650° C. Using temperatures in the stated range to produce the permanent filters makes it possible to make said filters sufficiently stable, in particular to allow a self-supporting embodiment of the permanent filters. Microporosity of the globular substrate grains is obtained as a function of temperature. The higher the temperature, the lower the microporosity.

It is advantageous for the permanent filter to be produced by sintering with a sintering time in a range from around 150 minutes to around 330 minutes. The sintering time preferably amounts to around 180 minutes to around 300 minutes. Sintering of the globular substrate grains for a sintering time in the stated range ensures the necessary high quality of the permanent filter.

In particular to improve the strength of the permanent filter, it is advantageous for the permanent filter to be produced by adding sintering additives to the globular substrate grains prior to sintering. To convert the globular substrate grains forming "microceramics" into an adhesively bonded structure, they have to be pressed and sintered, as described, at very high sintering temperatures. However, a very good adhesive bond may also be achieved in particular if sintering additives are added to the globular substrate grains. The addition of sintering additives allows the permanent filter to be formed by sintering at relatively low temperatures. In particular, the colour of the permanent filter may then for example also be predetermined as a function of the selected sintering additives.

It is favourable for the permanent filter to be produced with sintering additives in the form of sinter-active aluminium oxide powder, preferably around 10 to around 30 weight percent, and/or sinter-active titanium oxide, magnesium oxide, silicon oxide, iron oxide, manganese oxide, nickel oxide, cobalt oxide, chromium oxide and/or rare earth oxides. The addition of one or more of the stated materials allows the formation of an optimum adhesive bond of the globular substrate grains to yield a stable permanent filter.

It is particularly favourable for the permanent filter to be produced by using around 1 to 1.5 weight percent of titanium oxide ($TiO_2$) and/or around 0.2 weight percent of magnesium oxide (MgO). Such an addition of sintering additives allows the formation of a permanent filter with the desired properties.

The permanent filter preferably contains a proportion of globular substrate grains of around 75 to around 85 weight percent and a proportion of sintering additives of around 15 to around 25 weight percent. Permanent filters formed in this way have very good and uniform porosity.

The stability of the permanent filter may be further improved if the permanent filter is produced by grinding the globular substrate grains prior to sintering. In particular, grinding may proceed after addition of a sintering additive. In this way, it is possible to ensure optimum bonding of the globular substrate grains on sintering.

In particular, it is favourable for the permanent filter to be produced by adding a binder after grinding the mixture of globular substrate grains and the sintering additive. In this way, cohesion, i.e. primary dimensional stability, of the filter blank may be achieved.

According to a further preferred embodiment of the invention, provision may be made for the permanent filter to be produced by shaping the mixture after addition of the binder in a pressing tool, removing the binder, preferably thermally, and subsequent sintering. A blank pressed in this way and already bound using the binder and which has its final shape and microconfiguration imparted by sintering has the desired reproducible filter properties.

It is advantageous for the permanent filter to be produced by fractionating the spray-dried primary grains by screening. This has the advantage that practically only primary grains of a predetermined defined size are used for calcination and the subsequent sintering process. In this way, a uniform distribution of equally sized or substantially equally sized globular substrate grains may be achieved, which ensures a defined porosity for the permanent filter.

Flow rates necessary for a permanent filter of a sterilization container may be achieved in particular if grain sizes of the primary grain fraction fractionated by the screening have a grain diameter in a range from around 90 μm to around 150 μm.

The quality of the permanent filter can be further improved if it is produced by spray drying the suspension with the addition of an organic binder. In particular it is favourable for the organic binder to be polyvinyl alcohol or polyacrylate.

If in particular the ceramic powder is zirconium oxide, it is favourable for this to be stabilized with MgO, CaO, $Y_2O_3$, $CeO^2$ or mixtures of the stated compounds.

It is advantageous for the permanent filter to be provided with a hydrophobic coating. This prevents the permanent filter from becoming saturated with water.

A good water-repellent action can be achieved, for example, in that the hydrophobic coating covers a surface of the permanent filter.

To prevent the permanent filter from becoming wholly saturated with water, it is favourable for the hydrophobic coating to be applied over the entire volume of the permanent filter.

Hydrophobic coating of the permanent filter can be achieved simply and inexpensively if the hydrophobic coating contains or is siloxane and/or Teflon. In particular, a coating containing or consisting of Teflon is stable even when cleaning agents are used which have a pH value greater than 10.

The present invention further relates to a medical sterilization container, in particular for receiving and storing objects to be sterilized, with a container bottom part and a container top part for closing the container bottom part in a closed position of the sterilization container, the sterilization container defining a container interior, which is delimited by the container bottom part and by the container top part, and the container bottom part and/or the container top part having a gas exchange orifice, which is closed with a permanent filter, wherein the permanent filter is made from a ceramic and wherein the ceramic is made from globular substrate grains.

A sterilization container with one of the above-described ceramic permanent filters allows reliable, airtight, germ-proof storage of objects, in particular implants and surgical instruments in the container interior. In addition, filter changing is not required. The ceramic permanent filter may additionally itself be sterilized.

The present invention further relates to a method for producing a permanent filter for a medical sterilization container, wherein the permanent filter is produced from a ceramic material by sintering and wherein globular substrate grains are used as the ceramic material.

It is possible in this way to produce ceramic permanent filters which are sufficiently bioinert and biocompatible to be able to serve durably in particular as filters for medical sterilization containers. Moreover, a porosity and a pore size of the permanent filter may be adjusted in a defined manner. Furthermore, the handling of globular substrate grains is relatively simple. In addition, the sterilization conditions may, as described above, be fulfilled without difficulty by such a ceramic permanent filter. Overall, a uniform filter may be formed, i.e. with only slight differences between the pores defined thereby with regard to size and shape.

It is favourable for the substrate grains to be produced by dispersing and deagglomerating ceramic powder in aqueous suspension to produce individual primary grains, spray drying the suspension containing the primary grains and calcining the primary grains to yield secondary grains, which form the globular substrate grains. In particular, calcination allows the formation of globular substrate grains of a defined size. Since a specific permeability is needed for the minimum throughput of air and hot steam through the permanent filter, the secondary grains needed for this purpose are produced in the desired size in a simple and reproducible manner.

It is advantageous for aluminium oxide ($Al_2O_3$), zirconium oxide ($ZrO_2$), titanium dioxide ($TiO_2$), mullite, silicate, kaolin or any desired mixture thereof to be used as the ceramic powder. These materials have the desired properties with regard to the bioinertness and biocompatibility required for the permanent filter in order in this way to allow sterilizability of the permanent filter.

Moreover it is advantageous for aluminium oxide ($Al_2O_3$) to be used in the form of γ-aluminium oxide (γ-$Al_2O_3$). In a next method step, particularly stable α-aluminium oxide (α-$Al_2O_3$) may be formed from this starting material. This aluminium oxide modification is highly stable in particular for forming the permanent filter.

Furthermore, it is favourable for calcination to proceed at temperatures of at least around 1100° C. In particular, it is advantageous for calcination to proceed in a temperature range from around 1300° C. to around 1500° C. It is favourable for calcination to be performed at around 1350° C. Performing calcination at these temperatures makes it possible to form high-quality α-aluminium oxide.

To form a durably stable permanent filter, it is favourable for globular substrate grains to be sintered for this purpose at temperatures in the range from around 1350° C. to around 1700° C. It is favourable for sintering to proceed in a temperature range from around 1390° C. to around 1650° C. Sintering at these temperatures makes it possible to form sufficiently stable permanent filters, in particular self-supporting permanent filters may be reliably produced in this way.

Preferably, sintering proceeds for a sintering time in a range from around 150 minutes to around 330 minutes. It is favourable for the sintering time to amount to from around 180 minutes to around 300 minutes. In this way, high-quality permanent filters can be produced.

To improve the stability and strength of the permanent filter it is favourable for sintering additives to be added to the globular substrate grains prior to sintering. Sintering additives improve the adhesive bond of the globular substrate grains. In addition, when sintering additives are used, lower sintering temperatures are sufficient to form a durably stable permanent filter.

It is favourable for sinter-active aluminium oxide powder, preferably around 10 to around 30 weight percent, and/or sinter-active titanium oxide, magnesium oxide, silicon oxide, iron oxide, manganese oxide, nickel oxide, cobalt oxide, chromium oxide and/or rare earth oxides to be used as sintering additives. Through the addition of one or more of these materials, an optimum adhesive bond of the globular substrate grains may be formed to produce a stable permanent filter. In particular, chromium oxide and rare earth oxides allow the permanent filter to be given a desired colour. Thus, the permanent filter may in particular be durably distinguished if necessary.

Advantageously, around 1 to 1.5 weight percent of titanium oxide ($TiO_2$) and/or around 0.2 weight percent of magnesium oxide (MgO) are used. Adding these sintering additives makes it possible to produce a permanent filter with the necessary properties.

According to a further preferred variant of the method according to the invention, it is favourable for a proportion of globular substrate grains to amount to around 75 to around 85 weight percent after sintering and a proportion of the sintering additives to amount to around 15 to around 25 weight percent. Permanent filters of this composition have very good, uniform porosity. They are determined substantially by the selected globular substrate grains, the properties of which are masked to only a limited degree by the sintering additives.

The globular substrate grains are favourably ground, in particular after the addition of a sintering additive. In this way, the globular substrate grains may be optimally bonded on sintering.

To improve the stability of the filter, it is advantageous for at least one binder to be added after grinding of the mixture of the globular substrate grains and the sintering additive. In this way, prior to sintering there is produced, by means of a pressing tool, a filter blank which already coheres well. Subsequent, preferably thermal, removal of the binder and then sintering of the filter blank makes it possible to form permanent filters with the desired properties.

According to a further preferred variant of the method according to the invention, provision may be made for the mixture to be shaped in a pressing tool after addition of the binder, the at least one binder to be removed, preferably thermally, and for sintering to be performed. In the pressing tool the mixture of globular substrate grains and the binder may be shaped to form a filter blank. The binder may then be removed, for example by heating, and by sintering the filter blank may be produced in the final shape of the permanent filter with the desired microconfiguration of pores.

Fractionation of the spray-dried primary grains is preferably performed by screening. In this way, it is possible simply to select from the spray-dried primary grains those which have a predetermined defined size in order to form pores of the permanent filter in the desired size and number after calcination and the subsequent sintering process.

It is advantageous for a primary grain fraction with a grain diameter in a range from around 90 μm to around 150 μm to be fractionated by screening. In this way, the flow rates required for a sterilization container may be predetermined.

Spray drying may be carried out simply and improve the quality of the permanent filter, if spray drying of the suspension proceeds with the addition of an organic binder. In particular, polyvinyl alcohol or polyacrylate are suitable as organic binders.

To produce durably stable permanent filters from zirconium oxide, it is favourable for the zirconium oxide to be stabilized with MgO, CaO, $Y_2O_3$, $CeO_2$ or mixtures of the stated compounds.

Production of the permanent filter may be further simplified and costs further reduced if the permanent filter is self-supporting, without a support element.

It is advantageous for the permanent filter to be provided with a hydrophobic coating. This prevents the permanent filter from becoming saturated with water.

A good water-repellent action can be achieved, for example, in that the hydrophobic coating covers a surface of the permanent filter.

To prevent the permanent filter from becoming wholly saturated with water, it is favourable for the hydrophobic coating to be applied over the entire volume of the permanent filter.

Hydrophobic coating of the permanent filter can be achieved simply and inexpensively if the hydrophobic coating is formed by application of siloxane and/or Teflon. In particular, a coating containing or consisting of Teflon is stable even when cleaning agents are used which have a pH value greater than 10.

FIG. 1 is schematic representation of a sterilization container 10, which comprises a trough-like container bottom part 12 and a container top part 14 in the form of a lid. The container top part 14 is configured to close the container bottom part 12 in a closed position, not shown, of the sterilization container 10. The sterilization container 10 defines a container interior 16, which is defined by the container bottom part 12 and the container top part 14. These are sealed relative to one another in the closed position, for example by a seal arranged on an bottom side of the container top part 14 and resting on a peripheral edge 18 of the container bottom part 12.

On the container bottom part 12 a filter assembly 20 is arranged, as shown schematically in FIG. 1, which comprises a disc-shaped permanent filter 22 concealed in the filter assembly 20 by a cover 24. The permanent filter 22 takes the form of a ceramic permanent filter, the structure and production of which are described in greater detail below. The filter assembly 20 is configured and the permanent filter 22 is arranged therein in such a way that a gas exchange orifice, not shown in any greater detail and taking the form of a hole in the container bottom part 12, is covered completely and sealed by the permanent filter 22. This means that gas exchange between the surrounding environment of the sterilization container 10 and the container interior 16 is only possible through the permanent filter 22 in the closed position.

Alternatively or in addition, as shown schematically in dashed lines on the container top part in FIG. 1, a gas exchange orifice 26 may also be arranged or formed in the container top part 14, which gas exchange orifice may then be closed by the permanent filter 22, for example with a filter assembly 20 comprising the permanent filter 22.

Figure 2:
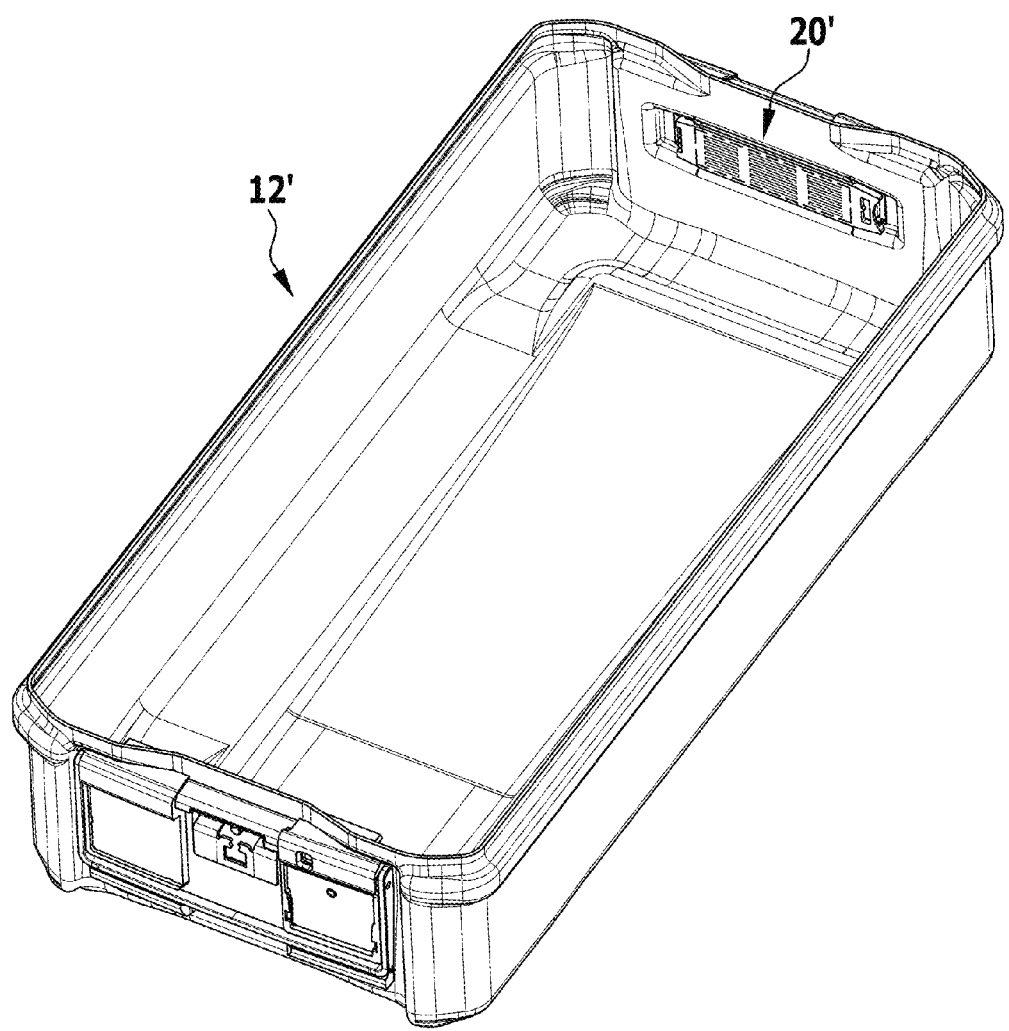
FIG. 2: is a perspective schematic representation of a second exemplary embodiment of a sterilization container with a permanent filter.
Figure 3:
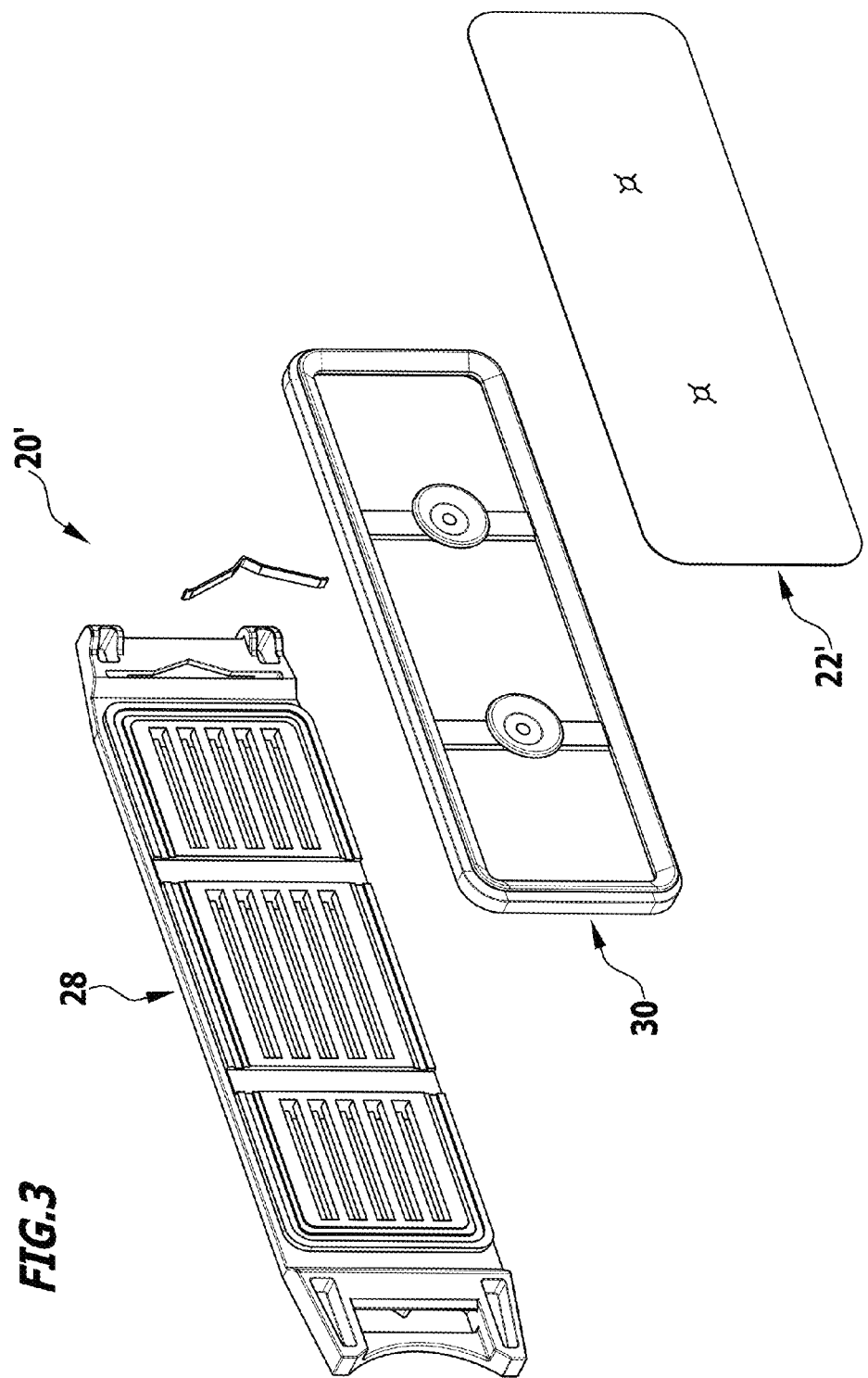
FIG. 3: is a schematic exploded representation of the filter assembly shown in FIG. 2 with a ceramic permanent filter.

FIG. 2 is a schematic representation of a second variant of a container bottom part 12'. At one end face thereof, a variant of a filter assembly 20' is arranged, which closes a substantially rectangular gas exchange orifice. The filter assembly 20' comprises a cover 28, a supporting frame 30 and a substantially rectangular permanent filter 22', which has no through holes. It may be held clamped between the cover 28 and the supporting frame 30.

The permanent filters 22 and 22' are made from a ceramic material by sintering. Globular substrate grains are used as the ceramic material. These are produced by dispersing and deagglomerating a ceramic powder in aqueous suspension to produce individual primary grains. The suspension containing the primary grains is spray-dried and then the primary grains are calcined to produce secondary grains. The calcined secondary grains then form the globular substrate grains. These are spherical or substantially spherical or spheroidal.

Aluminium oxide ($Al_2O_3$), zirconium oxide ($ZrO_2$), titanium dioxide ($TiO_2$), mullite, silicate, kaolin or any desired mixture thereof is used as the ceramic powder.

Preferably, γ-aluminium oxide (γ-$Al_2O_3$) is used as the aluminium oxide ($Al_2O_3$). Calcining transforms γ-aluminium oxide (γ-$Al_2O_3$) into α-aluminium oxide (α-$Al_2O_3$). This aluminium oxide modification is markedly more stable than the γ-aluminium oxide modification. γ-Aluminium oxide is transformed into α-aluminium oxide at around 1050° C. However, volume shrinkage is associated with this phase transformation of the starting material. This volume shrinkage, i.e. the size reduction from the primary grains to the secondary grains, then finally defines the porosity of the permanent filter in the compound.

Calcination to produce the permanent filter preferably proceeds at temperatures of at least around 1100° C. It is advantageous for calcination to proceed in a temperature range from around 1300° C. to around 1500° C. Calcination favourably proceeds at around 1350° C.

The spray-dried primary grains may optionally be fractionated by screening. Ideally a primary fraction with a grain diameter in a range from around 90 μm to around 150 μm is separated out by screening and then used for further production of the permanent filter.

In particular, spray drying of the aqueous suspension proceeds with addition of an organic binder. For example, polyvinyl alcohol or polyacrylate may be used for this purpose.

For final shaping and configuration of the permanent filter in practically any desired shape, the mixture of globular substrate grains is firstly preferably ground. In addition, the globular substrate grains may also be ground prior to a sintering process.

The grinding step preferably proceeds after the addition of a sintering additive. Sintering additives are optionally added to the globular substrate grains prior to sintering. Sinter-active aluminium oxide powder is particularly suitable as a sintering additive, preferably around 10 to around 30 weight percent. Alternatively or in addition, sinter-active titanium oxide, magnesium oxide, silicon oxide, iron oxide, manganese oxide, nickel oxide, cobalt oxide, chromium oxide and/or rare earth oxides may also be used as sintering additives. For example, 1 to 1.5 weight percent of titanium oxide ($TiO_2$) and/or around 0.2 weight percent of magnesium oxide (MgO) are added to the globular substrate grains as sintering additives.

The permanent filter is formed preferably by using a mixture of globular substrate grains and sintering additives, wherein the proportion of the globular substrate grains after sintering amounts to around 75 to around 85 weight percent, the proportion of sintering additives amounting to around 15 to around 25 weight percent.

To simplify shaping of the permanent filter and to impart primary stability to a filter blank, after grinding at least one binder is added to the mixture of globular substrate grains and the sintering additive. This may be a conventional binder, which is thermally removable, for forming oxide ceramics.

The mixture of globular substrate grains, binder and sintering additives is preferably shaped in a pressing tool. Then the binder may be removed, for example thermally by heating the filter blank.

In a final step the filter blank is sintered. The sintering process preferably proceeds at temperatures of around 1350° C. to around 1700° C. High quality permanent filters may in particular be obtained at sintering temperatures in a range from around 1390° C. to around 1650° C.

A sintering time is preferably in a range from around 150 minutes to around 330 minutes. In particular, the sintering time may amount to around 180 minutes to around 300 minutes.

Instead of aluminium oxide, zirconium oxide may also be used as the ceramic powder to produce a permanent filter. For stabilization, MgO, CaO, $Y_2O_3$, $CeO_2$ or mixtures of the stated compounds are preferably used.

Specific examples are discussed in detail below to form porous ceramic permanent filters.

Ceramics made of aluminium oxide grains, so-called fused corundum, have a very largely irregular structure, as is clearly visible from the SEM images in FIGS. 7 and 8. FIG. 7 shows surfaces and FIG. 8 fracture facets of such ceramics in the stated magnifications.

Exemplary Embodiment A

The globular grains of the permanent filter are produced as follows:
  dispersing and deagglomerating ceramic powder in aqueous suspension;
  spray drying the suspension with the addition of an organic binder, for example polyvinyl alcohol or polyacrylate;
  heat-treating the spray-dried grain at high temperatures for the purpose of producing a "microceramic" in the form of globular substrate grains.

The use of aluminium oxide powder has proven particularly suitable. This may be either γ-$Al_2O_3$ or α-$Al_2O_3$. $ZrO_2$ (stabilized with MgO, CaO, $Y_2O_3$, $CeO_2$ or mixtures thereof), $TiO_2$, mullite or other $Al_2O_3$—$SiO_2$ compounds (silicates, kaolins or the like) may however also be used as globular substrate grains.

Figure 4:
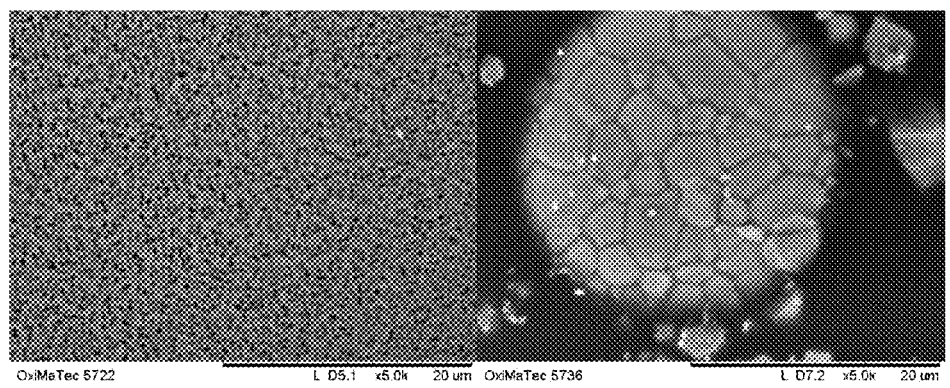
FIG. 4: $\gamma$-$Al_2O_3$ (1390° C., left), $\alpha$-$Al_2O_3$ (1390° C., right)
Figure 5:
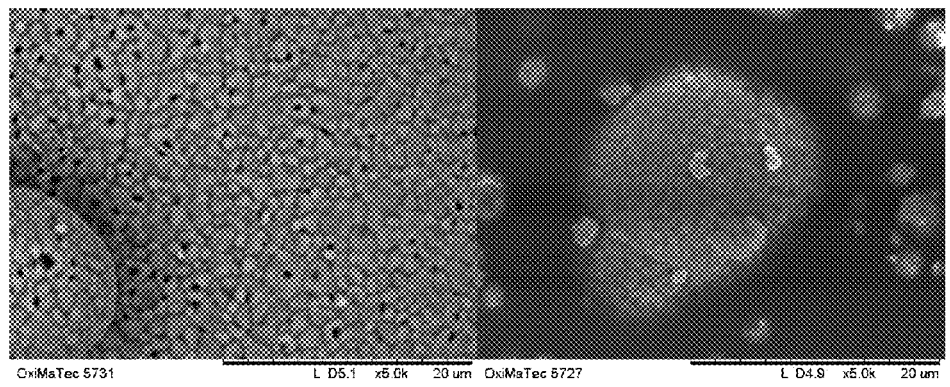
FIG. 5: $\gamma$-$Al_2O_3$ (1500° C., left), $\alpha$-$Al_2O_3$ (1500° C., right)

In this exemplary embodiment the permanent filter is based on sintered aluminium oxide grains as microceramics. If γ-$Al_2O_3$ is used, a markedly more fissured surface with corresponding porosity arises during calcination at 1350° C. or 1450° C. than is the case with calcination under identical conditions for α-$Al_2O_3$. Even at a sintering temperature of 1650° C., very fine pores may still be detected between the grains of the calcined γ-$Al_2O_3$. FIGS. 4 to 6 show SEM images, which show the differences in the microstructure. The respective parameters of the SEM images are indicated below said images.

To convert the microceramics into an adhesively bonded structure, they are pressed and sintered at extremely high sintering temperatures. However, a very good adhesive bond is also achieved if so-called sintering additives are added to the microceramics. Characteristic sintering additives are particularly preferred: aluminium oxide microceramics are preferably mixed with sinter-active aluminium oxide powder (10-30 wt. %) and deposited on the surface of the microceramics, so that the adhesive bond is ensured even at relatively low temperatures due to the formation of sinter necks.

Additional sintering activity is achieved by adding sinter-active titanium oxide, magnesium oxide or silicon dioxide as alloy components. Iron oxide, manganese oxide, nickel oxide, cobalt oxide, chromium oxide and rare earth oxides may however also be used as sintering aids. Some of the latter also give rise to another colour during the sintering process.

The addition of sintering additives as alloy components to the globular microceramics leads to a reduction in sintering temperature and simultaneously ensures a good adhesive bond. The sintering temperature on the one hand and the total porosity of the filter on the other hand may be influenced by the concentration thereof. A further variable influencing the porosity and the associated air permeability is the size of the sintered globular grains. In principle: the fewer sintering aids are available and the larger the globular microceramics, the higher the permeability of the filter and the higher the sintering temperatures to be applied. Relatively small microceramics ensure smaller pores in the ceramic bond and thus reduce the passage of air.

Exemplary Embodiment B

Ceramics made of aluminium oxide grains, so-called fused corundum, have a very largely irregular structure, as is clearly visible from the SEM images in FIGS. 7 and 8. FIG. 7 shows the surfaces and FIG. 8 fracture facets of such ceramics in the stated magnifications.

In contrast, the grain structure is based substantially on spherical polycrystalline particles. These spherical polycrystalline particles are produced as follows in a first process engineering step:
- dispersing and deagglomerating high purity $\gamma$-$Al_2O_3$;
- adding binder and spray drying;
- fractionating the spray-dried granular material and calcining at a temperature>1100° C., resulting in thermodynamically stable $\alpha$-$Al_2O_3$.

The spray drying process may influence the agglomerate size: if for example a two-fluid nozzle is used for the process, secondary grains of between 30 and 100 μm are preferably obtained. Coarse secondary grains are obtained by using a pressure nozzle for the spray drying process.

The spray drying process always results in a product with a given grain distribution. Subsequently, therefore, further narrowing of the desired fraction may be achieved by applying a screening process.

If the fractionated secondary grains of $\gamma$-$Al_2O_3$ are subjected to thermal treatment using a temperature of at least 1100° C., the thermodynamically stable $\alpha$-modification of the aluminium oxide is obtained. The higher the calcination temperature selected, the lower the surface porosity of the spherical polycrystalline particles. This is clearly revealed by the SEM images shown in FIG. 9 at a calcination temperature $T_{calc}$=1300° C. (top) and $T_{calc}$=1450° C. (bottom).

The particles sintered at 1300° C. still have discernible surface microporosity. In contrast, the $\gamma$-$Al_2O_3$ particles calcined at 1450° C. are impermeable.

Both variants may then be coated with sinter-active alumina particles with an average grain size of around 0.3 to around 0.4 μm. Depending on concentration and sintering temperature, the sintered secondary grains may thereby be sintered together.

Of assistance to sintering behaviour is the addition of sintering aids as alloy components, such as for example $SiO_2$, MgO and/or $TiO_2$.

Very good, uniform porosity is achieved in the sintered moulding if the proportion of sintered secondary grains is between 75 and 85 weight percent and the sintering additives are present in a concentration of from 15 to 25 weight percent. The main constituent in the sintering additive is $Al_2O_3$. The proportion of MgO relative to the total composition is a maximum of 1 weight percent and the proportion of $TiO_2$ is a maximum of 2.5 weight percent.

The SEM fracture images in FIG. 10 show the microstructure of the permanent filter produced in this way.

In contrast to ceramics based on the use of commercially obtainable electrically fused corundum, which is mixed with sintering aids, shaped and sintered, permanent filters produced as described have a very uniform pore structure over the entire filter due to the fractionated starting grains and their spheroidal shape. In the case of ceramics based on commercially obtainable electrically fused corundum, in addition to fine pores very coarse pores are frequently also found, i.e. overall a very non-uniform porosity.

Exemplary Embodiment C

The development of the porous ceramic filter is based substantially on the fact that firstly $\gamma$-$Al_2O_3$ is dispersed and spray-dried. After fractionation by screening of the spray-dried grain, the latter is subjected to calcination. In this calcination step the $\gamma$-$Al_2O_3$ is converted into the thermodynamically stable $\alpha$-modification. This is associated with a shrinkage process. Furthermore, it is possible with this step, depending on the level of the calcination temperature, to configure the surface properties of the secondary grain accordingly. The globular structure is retained. These secondary grains form the matrix for production of the filter. In test series V0500-V0504 it was possible to demonstrate that on the one hand a sinter-active aluminium oxide powder and additionally adding small quantities of titanium oxide and magnesium oxide as alloy components are helpful for reducing the sintering temperature and/or improving the adhesive bond. In this way, it is possible to achieve high flow rates in line with the target range.

Figure 12:
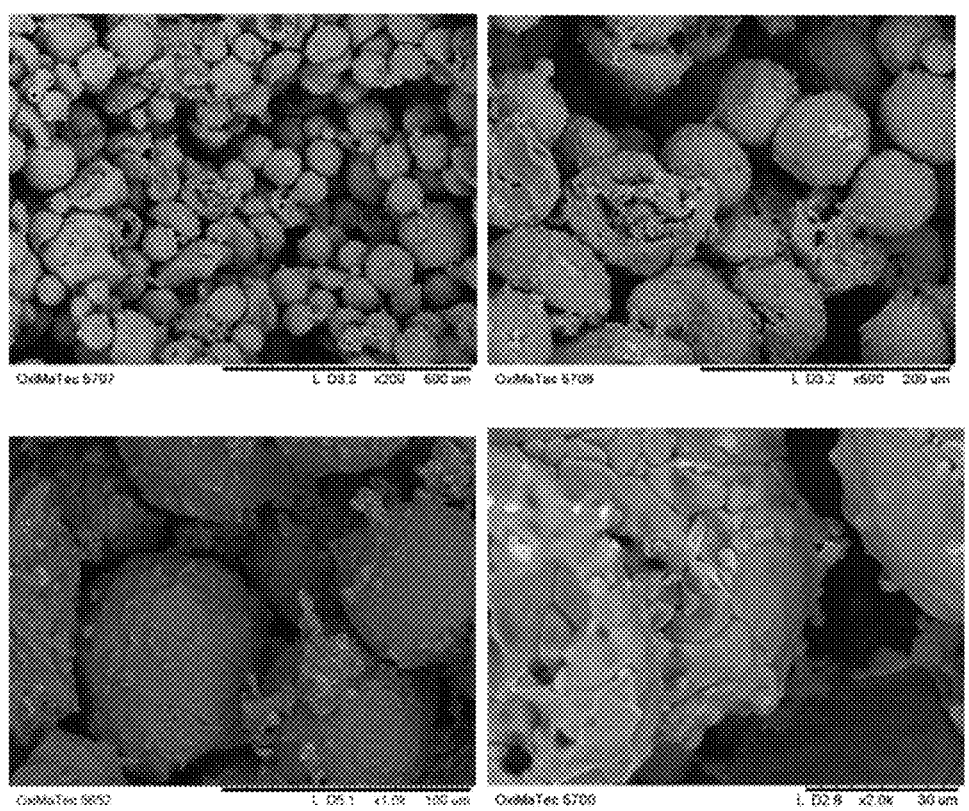
FIG. 12: SEM micrographs of samples from the pressing tool.
Figure 13:
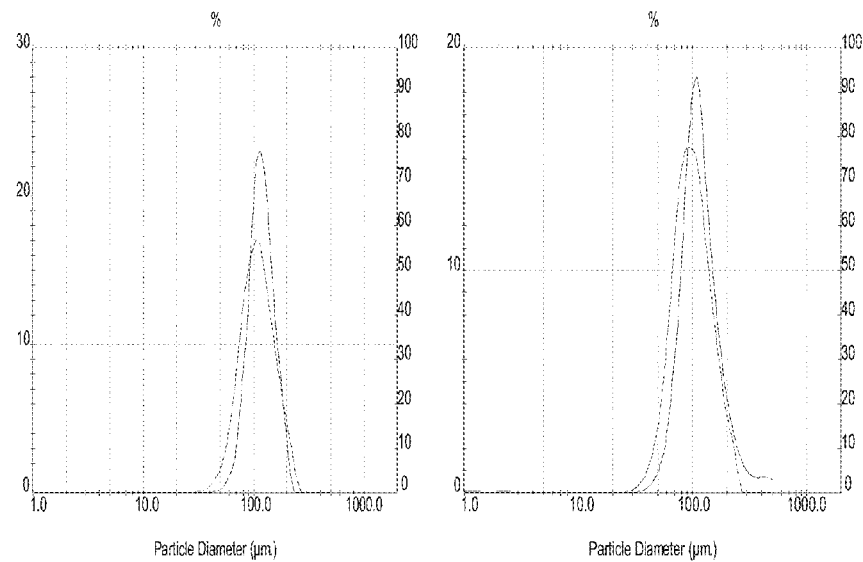
FIG. 13: Grain distribution of the screening fractions i) 150-90 μm (left) and ii) 106-90 μm (right)

SEM investigations of selected sintered mouldings are described in greater detail below.

a) SEM Investigations on V0500—Sintered at 1700° C./5 h
V0500 is based on the 150-90 μm secondary grain fraction, and has 15 weight percent of APA0.5 and 0.25 weight percent of $SiO_2$ in the material batch. The secondary grain fraction was calcined at 1350° C. Measured flow was 87 ml/sec*bar*cm². FIG. 11 shows SEM images of V0500.

b) SEM Investigations of First Samples from the Pressing Tool
Firstly, the 150-90 μm grain size fraction was calcined at 1450° C., then mixed with 15 weight percent APA0.5, 1.25 weight percent $TiO_2$ and 0.2 weight percent MgO and finally subjected to milling. Finally, the binder was then added, before this batch was shaped in the present pressing tool, the binder was removed and then the batch was sintered at 1650° C. for 3 hours. FIG. 12 shows corresponding SEM micrographs.

The calcination temperature used can influence on the one hand the stability of the secondary grains and on the other hand the surface finish. The lower the calcination temperature selected for the transformation of $\gamma$-$Al_2O_3$ into $\alpha$-$Al_2O_3$, the higher the remaining surface on the individual secondary grains. On the other hand, secondary grains sintered at a relatively low temperature are relatively easy to destroy on pressing. At a higher calcination temperature, the stability of the secondary grains increases. Moreover, a higher flow rate is expected with this formulation. To adjust the flow rates of the permanent filter, the following parameters are applied:
- screening fraction of the $\gamma$-$Al_2O_3$ secondary grains,
- calcination temperature for the $\gamma$-$Al_2O_3$ to $\alpha$-$Al_2O_3$ phase transformation,
- addition of the concentration of sinter-active $\alpha$-alumina as an alloy component,
- addition of sintering additives as an alloy component,
- sintering temperature.

Exemplary Embodiment D

To produce a permanent filter, a $\gamma$-alumina with corresponding grain distribution was processed, screened and the screened granular material was then appropriately calcined. Firstly, defined fractions are then calcined at different temperatures and subsequently mixed with alumina to increase the sintering activity. These batches were moreover doped with $SiO_2$ and MgO in the quantities permitted according to ISO 6474. In a series of test formulations, it was possible to increase the flow rates, and yet at around 30 ml/sec*bar*cm² the flow rate measured at Aesculap was ultimately still too low.

Granular material was produced from $\gamma$-$Al_2O_3$ by grinding. After spray drying the granular material was fractionated cleanly. Focus was placed on the classifications
i) 150-106 μm and
ii) 106-90 μm.

These fractions were then calcined at 1390° C.

Figure 14:
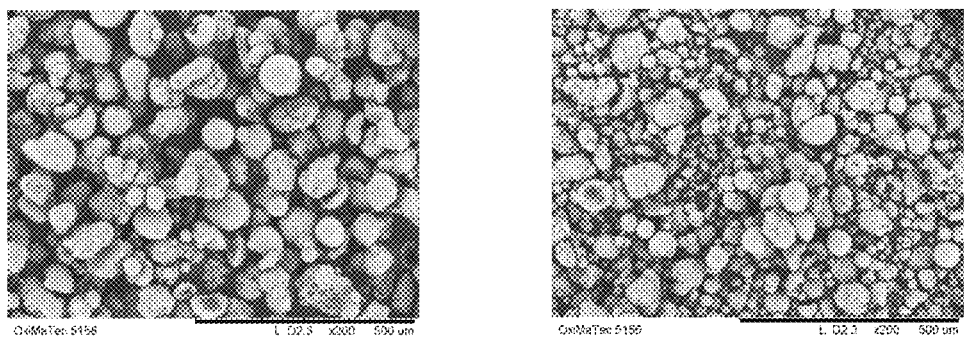
FIG. 14: Screening fraction 150-90 μm; left before calcination and right after calcination.
Figure 17:
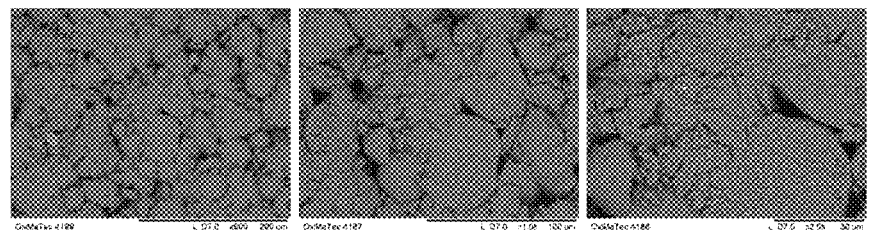
FIG. 17: V0453 surface (1450° C./5 h)
Figure 18:
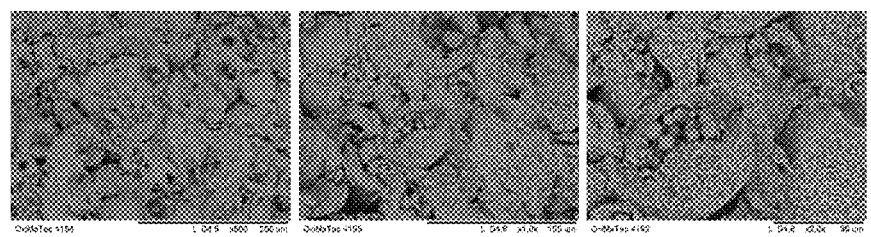
FIG. 18: V0453 fracture (1525° C./5 h)
Figure 19:
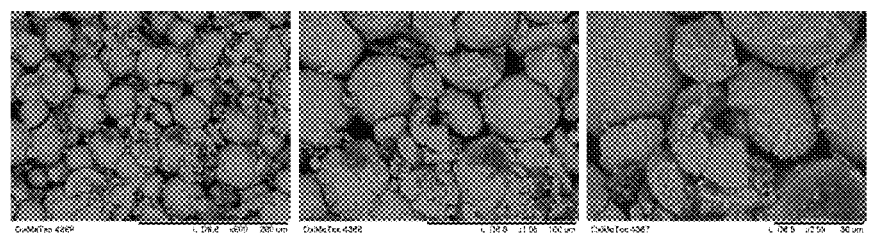
FIG. 19: V0458 surface (1580° C./5 h)
Figure 20:
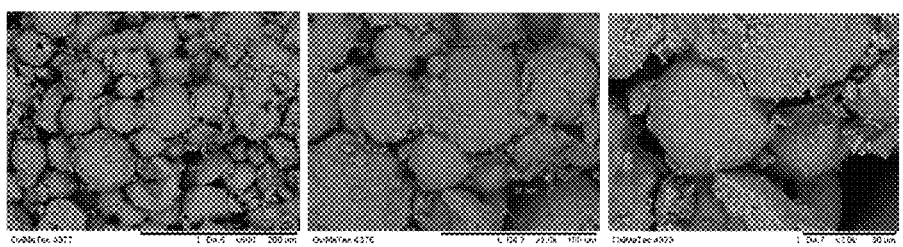
FIG. 20: V0458 fracture (1580° C./5 h)
Figure 21:
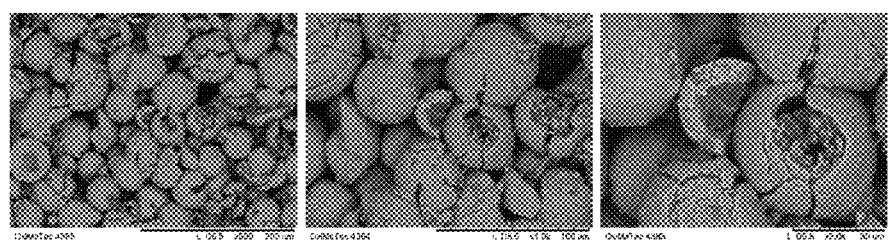
FIG. 21: V0459 surface (1580° C./5 h)
Figure 22:
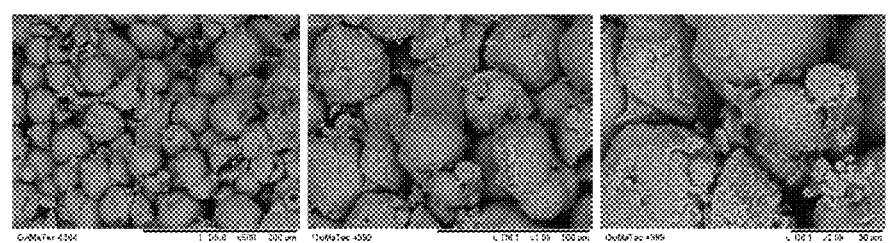
FIG. 22: V0459 fracture (1580° C./5 h)
Figure 23:
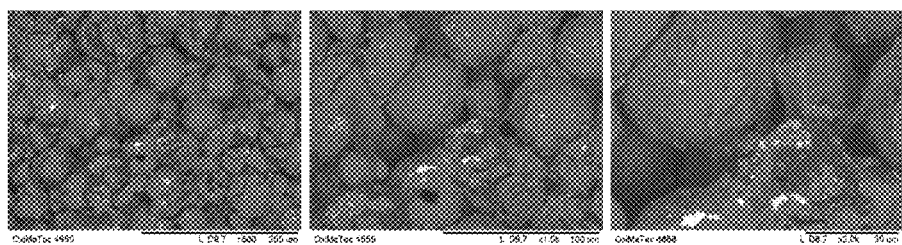
FIG. 23: V0480 surface (1600° C./5 h)
Figure 24:
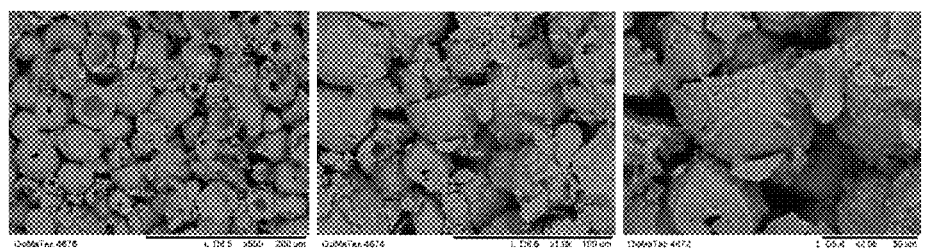
FIG. 24: V0480 fracture (1600° C./5 h)
Figure 25:
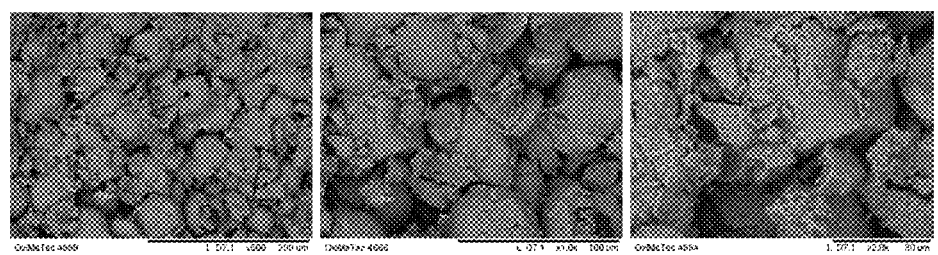
FIG. 25: V0480 fracture (1450° C./5 h).

Since shrinkage takes place during the $\gamma$- to $\alpha$-$Al_2O_3$ phase transformation, it was first determined how the granular material behaves in the grain distribution. FIG. 14 shows the granular material distribution of variant i) (left: blue=γ-$Al_2O_3$, red=α-$Al_2O_3$) and ii) (right: blue=γ-$Al_2O_3$, red=α-$Al_2O_3$).

Table 1 reproduces the grain distribution. FIG. 15 shows the SEM micrographs of the 150-90 μm screening fraction; FIG. 16 the 106-90 μm screening fraction.

TABLE 1

Grain distribution of the screening fractions before and after calcination

| | Fraction 150-90 μm | | Fraction 106-90 μm | |
| --- | --- | --- | --- | --- |
| | γ-$Al_2O_3$ | γ-$Al_2O_3$ | γ-$Al_2O_3$ | γ-$Al_2O_3$ |
| $d_{10}$ [μm] | 81 | 68 | 72 | 61 |
| $d_{50}$ [μm] | 115 | 107 | 111 | 98 |
| $d_{90}$ [μm] | 164 | 172 | 192 | 164 |

To produce a homogeneous mixture the sinter-active alumina may be dispersed in water and then mixed with the calcination product. One possible alternative is a dry method: dry mixing/grinding with 2% binder on a roller bed. The latter method has proven very efficient, since the sinter-active alumina becomes uniformly attached to the calcined coarse grains. FIG. 4 shows the pure calcination product (left) and the calcination product mixed with 15 weight percent APA0.5.

The various tests shows that the 106-90 μm fraction leads, after sintering with alumina and further dopants, to lower flow rates than is the case for the 150-90 μm fraction. Against this background, the batches based on this latter fraction were subjected to closer examination. Table 2 summarises the results.

TABLE 2

Chemical composition, flow rates and porosity

| Batch | Fraction [μm] | APA0.5 content [wt. %] | Doping | Sintering [° C./h] | Porosity [%] | OxiMaTec flow [ml/sec* bar * cm²] | Aesculap flow [ml/sec * bar * cm²] | Stability |
| --- | --- | --- | --- | --- | --- | --- | --- | --- |
| | 106-90 | 15 | 0.25% $SiO_2$ | 1700/5 | 32 | 250 | | not bad |
| V0500 | 150-90 | 15 | 0.25% $SiO_2$ | 1600/5 | | 45 | — | unsatisfactory |
| V0500 | 150-90 | 15 | 0.25% $SiO_2$ | 1700/5 | 33 | 360 | 87 | better |
| V0501 | 150-90 | 15 | — | 1600/5 | | 45 | | unsatisfactory |
| V0501 | 150-90 | 15 | — | 1700/5 | 29 | 290 | 105 | not bad |
| V0502 | 150-90 | 15 | 0.25% $TiO_2$ | 1600/5 | | 400 | | inadequate |
| V0502 | 150-90 | 15 | 0.25% $TiO_2$ | 1700/5 | 35 | 480 | 71 | better |
| V0503 | 150-90 | 15 | 1.25% $TiO_2$ | 1600/5 | | 350 | | better |
| V0503 | 150-90 | 15 | 1.25% $TiO_2$ | 1700/5 | 31 | 590 | 84 | not bad |
| V0504 | 150-90 | 15 | 0.25% $TiO_2$ + 0.2% MgO | 1700/5 | | 5 | 54 | very good |
| V0504 | 150-90 | 15 | 0.25% $TiO_2$ + 0.2% MgO | 1525/5 | | 400 | | good |

High flow rates with good sintered body stability are achieved at high sintering temperatures. Doping with MgO and $TiO_2$ in low concentrations leads to an enormous increase in sintering activity simultaneously combined with high air permeability.

According to the present results, a broader distribution of the pores in the coarse range is better than a narrow one. The 150-90 μm screening fraction allows flow rates to be achieved which are in the target range. Very good stability of the sintered mouldings is achieved if the batch is doped with titanium dioxide and magnesium oxide. This measure also allows the sintering temperature to be reduced. Batches without doping require a very high sintering temperature to achieve high flow rates and good stability of the mouldings.

With the present test results, it proved possible to achieve a desired flow rate. It would appear logical to perform further detailed optimization with variations in $TiO_2$ and MgO concentration in parallel with the process engineering conversion into an injection moulding batch. In this way, the sintering temperature may be further reduced under certain circumstances.

Exemplary Embodiment E

Here too, aluminium oxide agglomerates were produced via γ-$Al_2O_3$ and sintered with alumina or additional additives.

To achieve the desired flow quantity in the filter, it has been found that the agglomerates from the γ-alumina produced by the spray drying process should preferably be present in a specific fraction. Against this background, a pilot formulation with γ-$Al_2O_3$ was ground in the agitator, mixed with binder and then spray-dried in a very broad grain distribution. After spray drying the following screening fractions were produced:

>150 μm
150-106 μm
106-63 μm
63-45 μm
<45 μm

The individual grain fractions were then calcined in part at 1050° C. and at 1350° C. and thus converted into α-$Al_2O_3$.

All the material formulations exhibit air percolation; the flow rate is however very low in various samples and not measurable with the available measuring apparatus.

The highest flow rates are achieved if the 106-63 μm fraction is used with APA0.5 alumina and/or additionally with $SiO_2$ and/or MgO in the context of the admissible values according to IS06474 Part 1. The concentration of the alumina used as a sintering aid may influence the flow rate within certain limits. The sintering temperature used is mainly responsible for abrasion resistance. At sintering temperatures of 1525° C. and above, the stability of the grain bond becomes ever better.

The following table provides an overview of the material formulations used and their behaviour during sintering or the flow behaviour after sintering:

| | Grain fraction | Calcination temperature | Sintering | Formulation | ρ[g/cm³] | P [%] | Flow rate [ml/sec * bar * cm²] |
|---|---|---|---|---|---|---|---|
| γ-Al₂O₃ | <45 μm | — | 1390° C./5 h | pure | 2.10 | 47 | "bubbles" |
| | | | 1450° C./5 h | | 2.43 | 39 | "bubbles" |
| | | | 1525° C./5 h | | 2.62 | 34 | "bubbles" |
| γ-Al₂O₃ | 63-45 μm | — | 1390° C./5 h | pure | 2.05 | 49 | "bubbles" |
| | | | 1450° C./5 h | | 2.38 | 40 | "bubbles" |
| | | | 1525° C./5 h | | 2.54 | 36 | "bubbles" |
| γ-Al₂O₃ | 106-63 μm | — | 1390° C./5 h | pure | 2.35 | 41 | "bubbles" |
| | | | 1450° C./5 h | | 2.74 | 31 | "bubbles" |
| | | | 1525° C./5 h | | 2.81 | 30 | "bubbles" |
| V0451 | >150 μm | 1050° C. | 1390° C./5 h | 75 wt. % γ-Al₂O₃ + | 2.39 | 40 | "bubbles" |
| | | | 1450° C./5 h | 25 wt. % APA0.5 | 2.74 | 31 | "bubbles" |
| | | | 1525° C./5 h | | 2.95 | 26 | "bubbles" |
| V0452 | 150-106 μm | 1050° C. | 1390° C./5 h | 75 wt. % γ-Al₂O₃ + | 2.32 | 42 | "bubbles" |
| | | | 1450° C./5 h | 25 wt. % APA0.5 | 2.70 | 32 | "bubbles" |
| | | | 1525° C./5 h | | 2.89 | 28 | "bubbles" |
| V0453 | 106-63 μm | 1050° C. | 1390° C./5 h | 75 wt. % γ-Al₂O₃ + | 2.30 | 42 | "bubbles" |
| | | | 1450° C./5 h | 25 wt. % APA0.5 | 2.66 | 33 | "bubbles" |
| | | | 1525° C./5 h | | 2.85 | 29 | "bubbles" |
| V0454 | 63-45 μm | 1050° C. | 1390° C./5 h | 75 wt. % γ-Al₂O₃ + | 2.37 | 41 | "bubbles" |
| | | | 1450° C./5 h | 25 wt. % APA0.5 | 2.71 | 32 | "bubbles" |
| | | | 1525° C./5 h | | 2.90 | 27 | "bubbles" |
| V0455 | <45 μm | 1050° C. | 1390° C./5 h | 75 wt. % γ-Al₂O₃ + | 2.40 | 40 | "bubbles" |
| | | | 1450° C./5 h | 25 wt. % APA0.5 | 2.77 | 31 | "bubbles" |
| | | | 1525° C./5 h | | 2.97 | 26 | "bubbles" |
| V0456 | 150-106 μm | 1350° C. | 1390° C./5 h | 75 wt. % γ-Al₂O₃ + | 2.34 | 41 | 33 |
| | | | 1450° C./5 h | 25 wt. % APA0.5 | 2.53 | 37 | 13 |
| | | | 1525° C./5 h | | 2.68 | 33 | 13 |
| | | | 1580° C./5 h | | 2.71 | 32 | 40 |
| V0457 | 150-106 μm | 1350° C. | 1390° C./5 h | 85 wt. % γ-Al₂O₃ + | 2.16 | 46 | 53 |
| | | | 1450° C./5 h | 15 wt. % APA0.5 | 2.36 | 41 | 80 |
| | | | 1525° C./5 h | | 2.46 | 38 | 87 |
| | | | 1580° C./5 h | | 2.51 | 37 | 67 |
| V0458 | 106-63 μm | 1350° C. | 1390° C./5 h | 75 wt. % γ-Al₂O₃ + | 2.13 | 47 | 67 |
| | | | 1450° C./5 h | 25 wt. % APA0.5 | 2.43 | 39 | 67 |
| | | | 1525° C./5 h | | 2.44 | 39 | 60 |
| | | | 1580° C./5 h | | 2.29 | 43 | 147 |
| V0459 | 106-63 μm | 1350° C. | 1390° C./5 h | 85 wt. % γ-Al₂O₃ + | 1.96 | 51 | 153 |
| | | | 1450° C./5 h | 15 wt. % APA0.5 | 22.17 | 46 | 167 |
| | | | 1525° C./5 h | | 2.24 | 44 | 200 |
| | | | 1580° C./5 h | | 2.29 | 43 | 180 |
| V0460 | 63-45 μm | 1350° C. | 1390° C./5 h | 85 wt. % γ-Al₂O₃ + | 2.07 | 48 | "bubbles" |
| | | | 1450° C./5 h | 15 wt. % APA0.5 | 2.27 | 43 | 47 |
| | | | 1525° C./5 h | | 2.37 | 41 | 33 |
| V0461 | <45 μm | 1350° C. | 1390° C./5 h | 85 wt. % γ-Al₂O₃ + | 2.25 | 44 | "bubbles" |
| | | | 1450° C./5 h | 15 wt. % APA0.5 | 2.30 | 42 | "bubbles" |
| | | | 1525° C./5 h | | 2.66 | 33 | "bubbles" |
| V0462 | 106-63 μm | 1350° C. | 1390° C./5 h | 80 wt. % γ-Al₂O₃ + | 1.94 | 51 | 100 |
| | | | 1525° C./5 h | 20 wt. % APA0.5 | 2.22 | 44 | 107 |
| V0465 | 63-45 μm | 1350° C. | 1390° C./5 h | 80 wt. % γ-Al₂O₃ + | 2.26 | 43 | "bubbles" |
| | | | 1525° C./5 h | 20 wt. % APA0.5 | 2.59 | 35 | "bubbles" |
| V0463 | 106-63 μm | 1350° C. | 1390° C./5 h | 80 wt. % γ-Al₂O₃ + | 1.94 | 51 | 133 |
| | | | 1525° C./5 h | 19.95 wt. % APA0.5 + 0.05 wt. % SiO₂ | 2.20 | 45 | 160 |
| V0466 | 63-45 μm | 1350° C. | 1390° C./5 h | 80 wt. % γ-Al₂O₃ + | 2.06 | 48 | "bubbles" |
| | | | 1525° C./5 h | 19.95 wt. % APA0.5 + 0.05 wt. % SiO₂ | 2.40 | 40 | "bubbles" |
| V0464 | 106-63 μm | 1350° C. | 1390° C./5 h | 80 wt. % γ-Al₂O₃ + | 2.06 | 48 | 127 |
| | | | 1525° C./5 h | 19.95 wt. % APA0.5 + 0.05 wt. % SiO₂ + 0.04 wt. % MgO | 2.38 | 40 | 113 |
| V0467 | 63-45 μm | 1350° C. | 1390° C./5 h | 80 wt. % γ-Al₂O₃ + | 2.10 | 47 | "bubbles" |
| | | | 1525° C./5 h | 19.95 wt. % APA0.5 + 0.05 wt. % SiO₂ + 0.04 wt. % MgO | 2.46 | 38 | "bubbles" |
| V0480 | 106-63 μm | 1350° C. | 1450° C./5 h | 80 wt. % γ-Al₂O₃ + | 2.24 | 44 | 27 |
| | | | 1525° C./5 h | 19.95 wt. % APA0.5 + | 2.36 | 41 | 127 |
| | | | 1600° C./5 h | 0.2 wt. % SiO₂ + 0.2 wt. % MgO | 2.43 | 39 | 120 |
| V0481 | 63-45 μm | 1350° C. | 1525° C./5 h | 80 wt. % γ-Al₂O₃ + | 2.41 | 39 | "bubbles" |
| | | | 1600° C./5 h | 19.95 wt. % APA0.5 + 0.2 wt. % SiO₂ | 2.63 | 34 | "bubbles" |
| V0482 | 63-45 μm | 1350° C. | 1525° C./5 h | 80 wt. % γ-Al₂O₃ + | 2.57 | 35 | "bubbles" |
| | | | 1600° C./5 h | 19.95 wt. % APA0.5 + 0.2 wt. % SiO₂ + 0.2 wt. % MgO | 2.63 | 34 | "bubbles" |

Selected SEM images relating to the material formulations used are shown in FIGS. 17 to 25 below:

In the tests performed, it was always possible to achieve a high flow rate when using the 106-63 μm fraction. The higher the sintering temperature, the more the fine-grained structure disappears.

On the other hand, the components with a high sintering temperature have pores within the hollow grains which are produced in the spraying process.

As the sintering temperature increases, the abrasion resistance also increases. In the tests performed, no significant influence of doping by $SiO_2$ and/or MgO could be identified. The doped bodies tend to exhibit somewhat higher stability.

It is also apparent from the SEM micrographs that pure $\gamma\text{-}Al_2O_3$ is likewise less suitable for a high flow rate than an alumina only calcined at 1050° C. This is related to the fact that the secondary grains are crushed during shaping and thus the pore channels are narrowed. This is particularly clearly visible in the fracture images in FIG. 18.

Optional Hydrophobization of the Permanent Filters:

The above-described permanent filters may moreover optionally be provided with a siloxane coating, in order to reduce markedly the hydrophilicity of the permanent filters, which without coating is very pronounced.

The siloxane coating is produced by applying a siloxane layer to a newly produced permanent filter. This may optionally be heat-treated, or so to speak "stoved", at a temperature of at least 150° C.

Ceramic permanent filters coated in this way exhibit very good hydrophobicity in the water penetration test with fuchsin solution.

Investigations for corrosion resistance of the siloxane coating revealed good resistance in the alkaline range up to a pH value of approx. 10. In the case of highly alkaline cleaning agents, as used to clean the filters prior to sterilization, the layer exhibits marked corrosion phenomena after around just one hour of treatment, however.

Although the hydrophobization layer of siloxane is extremely thin, air percolation may be observed to have a lower volumetric flow rate than in the uncoated filters.

Given the corrosion problems of siloxane coatings in the highly alkaline range, which may lead over time to a reduction in hydrophobising action, a hydrophobic coating containing Teflon was proposed as an alternative. Teflon is known to be an extremely corrosion-resistant material.

To coat new ceramic permanent filters with Teflon, a micronised Teflon powder is used. However, this can be dispersed only with relative difficulty and may only be deposited on the surface of the filters. This coating does however adhere very well to the surface of the filters and is highly resistant, in particular to alkaline cleaning agents, even at a pH value greater than 10.

As an alternative to the described micronised Teflon powder, a Teflon emulsion may also be used for coating which is used for coating textiles. A hydrophobic coating of the permanent filters may thus likewise be formed. In particular, the Teflon emulsion makes it possible to achieve hydrophobization of entire permanent filters. In this case, it should be noted that, as the concentration of the Teflon emulsion increases, air permeability decreases. Permeability was investigated using cylindrical permanent filter samples. The following values were obtained:

| Dilution of the Teflon emulsion | Flow rate |
|---|---|
| 1:50 | 35 ml/s · bar · cm$^2$ |
| 1:10 | 25 ml/s · bar · cm$^2$ |
| 1:5 | 20 ml/s · bar · cm$^2$ |

As a result of the Teflon coating applied in the described manner, even after 2 h of boiling in cleaning solution no corrosion could be identified. However, the Teflon coating reduces air percolation through the permanent filter in comparison with the uncoated filter. The higher the concentration of the Teflon suspension, the more the air percolation is reduced.

To achieve the desired flow rate even with a permanent filter provided with a Teflon coating, a coarser pore structure is preferably selected for the permanent filter before it is hydrophobised with a Teflon coating. In this way, a desirable flow rate of at least 100 ml/s·bar·cm$^2$ may in particular be achieved.

What is claimed is:

1. A permanent filter for a medical sterilization container, comprising:
    a permanent filter made from a ceramic, and
    a hydrophobic coating applied over an entire volume of the permanent filter,
    wherein:
    the ceramic is made from globular substrate grains.

2. The permanent filter according to claim 1, wherein the permanent filter is self-supporting, without a support element.

3. The permanent filter according to claim 1, wherein the substrate grains are produced by:
    dispersing and deagglomerating ceramic powder in an aqueous suspension to produce individual primary grains,
    spray drying the suspension containing the primary grains, and
    calcining the primary grains to yield secondary grains, which form the globular substrate grains.

4. The permanent filter according to claim 3, wherein the ceramic powder comprises at least one of aluminium oxide ($Al_2O_3$), zirconium oxide ($ZrO_2$), titanium dioxide ($TiO_2$), mullite, silicate, and kaolin.

5. The permanent filter according to claim 4, wherein the ceramic powder is γ-aluminium oxide ($\gamma\text{-}Al_2O_3$).

6. The permanent filter according to claim 3, wherein the globular substrate grains are produced by calcining γ-aluminium oxide ($\gamma\text{-}Al_2O_3$) into α-aluminium oxide ($\alpha\text{-}Al_2O_3$).

7. The permanent filter according to claim 3, wherein the permanent filter is produced by the spray drying of the suspension containing the primary grains with an addition of an organic binder comprised of polyvinyl alcohol or polyacrylate.

8. The permanent filter according to claim 1, wherein the permanent filter is produced by adding sintering additives to the globular substrate grains prior to sintering.

9. The permanent filter according to claim 8, wherein the permanent filter contains a proportion of the globular substrate grains of around 75 to around 85 weight percent and a proportion of the sintering additives of around 15 to around 25 weight percent.

10. A medical sterilization container for receiving and storing objects to be sterilized, comprising:
    a container bottom part,
    a container top part for closing the container bottom part in a closed position of the sterilization container, a container interior delimited by the container bottom part and the container top part, a gas exchange orifice disposed in at least one of the container bottom part and the container top part, and a permanent filter for closing the gas exchange orifice, wherein:

the permanent filter is made from a ceramic, a hydrophobic coating is applied over an entire volume of the permanent filter, and the ceramic is made from globular substrate grains.

11. A method for producing a permanent filter for a medical sterilization container, comprising:

producing the permanent filter from a ceramic material by sintering, and applying a hydrophobic coating over an entire volume of the permanent filter, wherein globular substrate grains are used as the ceramic material.

12. The method according to claim 11, wherein the substrate grains are produced by:

dispersing and deagglomerating ceramic powder in an aqueous suspension to produce individual primary grains, spray drying the suspension containing the primary grains, and calcining the primary grains to yield secondary grains, which form the globular substrate grains.

13. The method according to claim 12, wherein the ceramic powder comprises at least one of aluminium oxide ($Al_2O_3$), zirconium oxide ($ZrO_2$), titanium dioxide ($TiO_2$), mullite, silicate, and kaolin.

14. The method according to claim 13, wherein the ceramic powder is aluminium oxide ($Al_2O_3$) in the form of γ-aluminium oxide (γ-$Al_2O_3$).

15. The method according to claim 12, wherein γ-aluminium oxide (γ-$Al_2O_3$) is transformed into α-aluminium oxide (α-$Al_2O_3$) by calcination.

16. The method according to claim 12, wherein calcination proceeds at temperatures of at least around 1100° C., in particular in a range from around 1300° C. to around 1500° C.

17. The method according to claim 12, wherein fractionation of the spray-dried primary grains proceeds by screening.

18. The method according to claim 12, wherein the spray drying of the suspension proceeds with an addition of an organic binder comprised of polyvinyl alcohol or polyacrylate.

19. The method according to claim 11, wherein the permanent filter is formed by the sintering of the globular substrate grains at temperatures in the range from around 1350° C. to around 1700° C.

20. The method according to claim 11, wherein the sintering proceeds for a sintering time in a range from around 150 minutes to around 330 minutes.

21. The method according to claim 11, wherein sintering additives are added to the globular substrate grains prior to the sintering.

22. The method according to claim 21, wherein at least one of sinter-active aluminium oxide powder, around 10 to around 30 weight percent, and sinter-active titanium oxide, magnesium oxide, silicon oxide, iron oxide, manganese oxide, nickel oxide, cobalt oxide, chromium oxide and rare earth oxides are used as the sintering additives.

23. The method according to claim 22, wherein at least one of around 1 to 1.5 weight percent titanium oxide ($TiO_2$) and around 0.2 weight percent magnesium oxide (MgO) are used as the sintering additives.

24. The method according to claim 21, wherein a proportion of the globular substrate grains amounts to around 75 to around 85 weight percent after the sintering and a proportion of the sintering additives amounts to around 15 to around 25 weight percent.

25. The method according to claim 11, wherein the permanent filter is self-supporting, without a support element.

\* \* \* \* \*